(12) United States Patent
Oliveira et al.

(10) Patent No.: US 11,306,058 B2
(45) Date of Patent: Apr. 19, 2022

(54) CRYSTALLINE FORM OF N-BUTYLDEOXYGALACTONOJIRIMYCIN

(71) Applicant: IDORSIA PHARMACEUTICALS LTD, Allschwil (CH)

(72) Inventors: Vitor Oliveira, Allschwil (CH); Ivan Pogorelic, Basel (CH); Jean-Paul Roduit, Sierre (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 110 days.

(21) Appl. No.: 16/618,036

(22) PCT Filed: May 31, 2018

(86) PCT No.: PCT/EP2018/064365
§ 371 (c)(1),
(2) Date: Nov. 27, 2019

(87) PCT Pub. No.: WO2018/220131
PCT Pub. Date: Dec. 6, 2018

(65) Prior Publication Data
US 2020/0140385 A1 May 7, 2020

(30) Foreign Application Priority Data
Jun. 1, 2017 (WO) ................ PCT/EP2017/063287

(51) Int. Cl.
| C07D 211/40 | (2006.01) |
| C07D 211/46 | (2006.01) |
| A61K 9/48 | (2006.01) |
| A61P 3/06 | (2006.01) |
| A61P 43/00 | (2006.01) |
| A61P 25/00 | (2006.01) |
| A61P 35/00 | (2006.01) |
| A61K 31/445 | (2006.01) |

(52) U.S. Cl.
CPC .......... C07D 211/40 (2013.01); A61K 9/4858 (2013.01); *C07B 2200/13* (2013.01)

(58) Field of Classification Search
CPC .. C07D 211/40; C07D 211/46; A61K 9/4858; A61K 31/445; C07B 2200/13; A61P 43/00; A61P 3/06; A61P 35/00; A61P 25/00
See application file for complete search history.

(56) References Cited

U.S. PATENT DOCUMENTS

| 6,291,657 B1 | 9/2001 | Platt et al. |
| 6,583,158 B1 | 6/2003 | Fan et al. |
| 2014/0243369 A1 | 8/2014 | Attolino et al. |

FOREIGN PATENT DOCUMENTS

| EP | 0 536 402 | 4/1993 |
| WO | WO 1994/026714 | 11/1994 |
| WO | WO 1999/062517 | 12/1999 |
| WO | WO 2002/055498 | 7/2002 |
| WO | WO 2004/054975 | 7/2004 |
| WO | WO 2006/037069 | 4/2006 |
| WO | WO 2006/125141 | 11/2006 |
| WO | WO 2007/014327 | 2/2007 |
| WO | WO 2007/123403 | 11/2007 |
| WO | WO 2009/001097 | 12/2008 |

OTHER PUBLICATIONS

Miller, J.J., "Progress in the understanding and treatment of Fabry disease." Biochimica et Biophysica Acta (BBA)—General Subjects 1864.1 (2020): 129437.*
Platt, F. M. "Emptying the stores: lysosomal diseases and therapeutic strategies." Nature Reviews Drug Discovery 17.2 (2018): 133.*
ChemIDplus, "Chemical information with searchable synonyms, structures, and formulas" Name: Polydimethylsiloxane, RN: 9016-00-6, *U.S. National Library of Medicine*, 1 page (2020).
Griesser, U.J., "The Importances of Solvates," Chapter 8, *Polymorphism in the Pharmaceutical Industry*, 19 pages (2006).
Guérard, N. et al., "Lucerastat, an iminosugar with potential as substrate reduction therapy for glycolipid storage disorders: safety, tolerability, and pharmacokinetics in healthy subjects," *Orphanet Journal of Rare Diseases*, vol. 12(9): 1-10 (2017).
Guérard, N. et al., "Lucerastat, an Iminosugar for Substrate Reduction Therapy: Tolerability, Pharmacodynamics, and Pharmacokinetics in Patients With Fabry Disease on Enzyme Replacement," *Clinical Pharmacology & Therapeutics*, vol. 103(4): 703-711 (2018).
Mistry, P.K. et al., "Glucocerebrosidase 2 gene deletion rescues type 1 Gaucher disease", *PNAS*, vol. 111(13): 4934-4939 (2014).
Perry, R. H., and Green, D. W., *Perry's Chemical Engineers' Handbook*, Seventh Edition, 2641 pages (1997).
Remington, "Pharmaceutical Manufacturing," Part 5, *The Science and Practice of Pharmacy*, 21st Edition, 5 pages (2005).
Rowe, R.C. et al., *Handbook of Pharmaceutical Excipients*, Fifth Edition, 945 pages (2006).
Asano et al., "In vitro inhibition and intracellular enhancement of lysosomal alpha-galactosidase A activity in Fabry lymphoblasts by 1-deoxygalactonojirimycin and its derivatives," *Eur J Biochem.* (2000); 267(13):4179-86.

\* cited by examiner

*Primary Examiner* — John M Mauro
(74) *Attorney, Agent, or Firm* — Hoxie & Associates LLC

(57) ABSTRACT

The invention relates to a crystalline form of [(2R,3S,4R,5S)-1-butyl-2-(hydroxymethyl)-piperidine-3,4,5-triol, processes for the preparation thereof, pharmaceutical compositions containing such a crystalline form, and its use as a medicament, especially as glycolipid biosynthesis inhibitor.

62 Claims, 1 Drawing Sheet

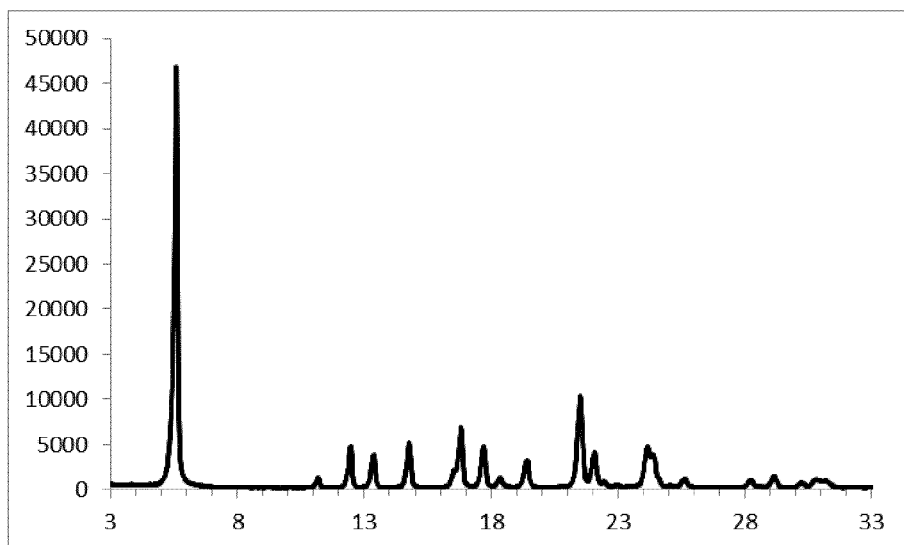

CRYSTALLINE FORM OF N-BUTYLDEOXYGALACTONOJIRIMYCIN

CROSS REFERENCE TO RELATED APPLICATIONS

This application is a United States Application under 35 U.S.C. 371 claiming benefit of PCT Application No. PCT/EP2018/064365, filed on May 31, 2018, which claims the benefit of PCT Application No. PCT/EP2017/063287, filed on Jun. 1, 2017, the contents of which are incorporated herein by reference.

The invention relates to a crystalline form of N-butyldeoxygalactonojirimycin, [(2R,3S,4R,5S)-1-butyl-2-(hydroxymethyl)piperidine-3,4,5-triol, hereinafter also referred to as "COMPOUND"]:

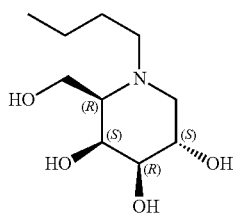

processes for the preparation thereof, pharmaceutical compositions comprising said crystalline form, pharmaceutical compositions prepared from such crystalline form, and its use as glycolipid biosynthesis inhibitor in a substrate reduction method for reducing the amount of glycolipids in a patient having a glycolipid storage disease or related disorder; especially in the treatment or prevention of Niemann-Pick type C disease, Gaucher disease types 1, 2 and 3, GM2 gangliosidoses (Tay-Sachs disease, Sandhoff disease, GM2 gangliosidosis AB variant), GM1 gangliosidosis, Fabry disease, Schindler disease, Smith-Lemly-Opitz syndrome, Tangier disease, mucolipidosis IV, mucopolysaccharidoses, GbA1-synucleopathies and syndromes thereof, Huntington's disease, polycystic kidney disease, Darier's disease, and Guillain-Barré syndrome.

In addition to the above-listed glycolipid storage diseases or related disorders, the potential utility of iminosugars in the treatment of the inflammatory components of human malignancies; infectious diseases such as urinary tract infection; neuronal disorders and neurodegenerative processes such as Alzheimer's disease, epilepsy, Parkinson's disease and syndromes thereof, stroke, spinal cord injuries, motor neuron disease (ALS), multiple sclerosis, and Lewy-Body dementia; inflammatory diseases and other disorders associated with macrophage recruitment and activation, including rheumatoid arthritis, Crohn's disease, asthma and sepsis; Krabbe disease; and cystic fibrosis has been proposed (see for example WO1999/062517, WO2002/055498, WO2006/037069, WO2006/125141, WO2007/014327, WO2007/123403, WO2009/001097).

N-butyldeoxygalactonojirimycin is known as inhibitor of glucosylceramide synthase (GCS; ceramide glucosyltransferase, UDP-glucose: ceramide glucosyltransferase, UDP-glucose:N-acylsphingosine D-glucosyltransferase, EC 2.4.1.80) (WO1994/026714). N-butyldeoxygalactonojirimycin is further known as inhibitor of non-lysosomal glucosylceramidase (GbA2, glucosylceramidase beta 2).

GCS inhibitors may find use in the treatment of glycolipid storage diseases, diseases associated with glycolipid accumulation, cancers in which glycolipid synthesis is abnormal, infectious diseases caused by microorganisms which use cell surface glycolipids as receptors, infectious diseases in which synthesis of glucosylceramide is essential or important, diseases in which excessive glycolipid synthesis occurs, neuronal disorders and neuronal injury.

GCS is an intracellular enzyme that catalyzes the assembly of uridine diphosphate-glucose and ceramide into the glycolipid, glucosylceramide. The role of GCS in regulating ceramide levels has been explored, since this molecule can induce apoptotic cell death. The role of GCS in maintaining cholesterol/glycolipid 'rafts', cell-surface membrane domains of specialized permeability and functionality that appear to be involved in a variety of signal transduction events, has also been investigated.

GCS is considered to be a target for treating certain human diseases. Glucosylceramide and structurally related glycolipids are stored in the lysosomes of patients with genetically inherited diseases, which result from a mutation in one of the essential glycolipid-degrading enzymes, e.g. Gaucher disease, GM2 gangliosidoses (Tay-Sachs disease, Sandhoff disease, GM2 gangliosidosis AB variant), GM1 gangliosidosis and Fabry disease. Glycolipid storage also occurs in some tissues with genetic storage diseases, such as Niemann-Pick type C disease, mucopolysaccharidoses, and mucolipidosis type IV (e.g. neuronal tissue), or with genetic organ-structure diseases, such as polycystic kidney disease (e.g. renal tissue). GCS inhibitors may be applied to reduce the rate of glycolipid synthesis in diseased cells so that there is less glycolipid present to be stored, a treatment approach termed substrate reduction therapy. Studies have demonstrated that GCS inhibitors can be used to reduce the glycolipid accumulation seen in cell and animal models of glycolipid storage. The GCS inhibitor N-butyldeoxynojirimycin (NB-DNJ) is indicated in the EU and the US for the treatment of Gaucher type 1 disease, and in the EU also for the treatment of Niemann-Pick disease Type C.

GbA2 is considered to be a target for treating certain human diseases. Deletion of the GbA2 gene in Gaucher disease mice (P. K. Mistry et al.; Proc Natl Acad Sci USA 2014; 111(13):4934-9) and Niemann-Pick type C mice markedly rescues their clinical phenotype, suggesting that GbA2 inhibitors can be used to treat Gaucher disease or other glycolipid storage diseases. Deletion of the GbA2 gene in Gaucher disease mice subjected to dextrane sulfate sodium induced colitis, or pharmacological inhibition of GbA2 in cystic fibrosis epithelial bronchial cells subjected to *Pseudomonas aeruginosa* infection both reduced the inflammatory response, suggesting that GbA2 inhibitors can be used to treat inflammatory diseases or the inflammation inherent to other diseases.

WO1994/026714 discloses COMPOUND, a process for the production thereof, and its use as glycolipid biosynthesis inhibitor. WO2004/054975 discloses an alternative process for the preparation of COMPOUND, wherein COMPOUND is disclosed to be obtained as a white to off white powder.

In a Phase Ib study in patients suffering from Fabry disease, treatment with COMPOUND on top of enzyme replacement therapy demonstrated a marked decrease in the plasma levels of metabolic substrates thought to be related to the development of the disease.

It has now been found that a particular crystalline form of COMPOUND may under certain conditions be found. Furthermore, certain manufacturing processes of said crystalline form of COMPOUND have been found. Said crystalline form of COMPOUND is novel and may have advantageous properties in view of the potential use of COMPOUND as active pharmaceutical ingredient. Such advantageous properties of COMPOUND may include lower amounts of impurities; pharmacologically more favourable impurity profile; better chemical and/or physical stability; good flow properties; good friability properties; less tendency to lump or to agglomerate upon storage, less coloration, low hygroscopicity; better reproducibiliy in manufacturing (for example better filtration parameters, better reproducibility of formation, and/or better sedimentation); and/or defined morphology and/or particle size, such as especially a particularly adapted particle size distribution suitable for direct blending for example with the pharmaceutically acceptable excipient lactose (such as especially anhydrous lactose). Such a direct blend of COMPOUND and one or more diluents such as especially lactose may lead to lower risk and/or higher yield upon scale up, and may exhibit low tendency of segregation and good galenical properties (such as better flow properties and/or less tendency to sticking, and/or better tapped and/or bulk density) and may be suitable for the preparation of solid pharmaceutical formulations (such as especially for filling of capsules). Such crystalline form of COMPOUND may be particularly suitable in a process of manufacturing certain pharmaceutical compositions in case a high drug load is required. In particular, depending on the target indication, a high dosage of COMPOUND of about 2 g per day may be required. In addition, iminosugars such as COMPOUND are known to have an unpleasant and long-lasting taste which requires efficient taste masking and/or encapsulation of the active ingredient when administered orally. Manufacturing processes of such crystalline form may be particularly simple, cost efficient, scalable, and transferable.

DESCRIPTION OF THE FIGURES

FIG. 1 shows the X-ray powder diffraction diagram of COMPOUND in a crystalline form 1 as obtained from Example 1. The X-ray diffraction diagram shows peaks having a relative intensity, as compared to the most intense peak in the diagram, of the following percentages (relative peak intensitites given in parenthesis) at the indicated angles of refraction 2theta (selected peaks from the range 3-30° 2theta are reported): 5.6° (100%), 12.4° (11%), 13.4° (9%), 14.8° (11%), 16.8° (16%), 17.7° (11%), 19.4° (7%), 21.5° (25%), 22.1° (9%), and 24.2° (11%).

For avoidance of any doubt, the above-listed peaks describe the experimental results of the X-ray powder diffraction shown in FIG. 1. It is understood that, in contrast to the above peak list, only a selection of characteristic peaks is required to fully and unambiguously characterize of the COMPOUND in the respective crystalline form of the present invention.

In the X-ray diffraction diagrams of FIG. 1 the angle of refraction 2theta (2θ) is plotted on the horizontal axis and the counts on the vertical axis.

DETAILED DESCRIPTION OF THE INVENTION

1) A first embodiment of the invention relates to a crystalline form of COMPOUND; characterized by the presence of peaks in the X-ray powder diffraction diagram at the following angles of refraction 2θ: 5.6°, 17.7°, and 21.5°.

It is understood, that the crystalline form according to embodiment 1) comprises COMPOUND in a crystalline form of the free base (i.e. not in form of a salt). Furthermore, said crystalline form may comprise non-coordinated and/or coordinated solvent. Coordinated solvent is used herein as term for a crystalline solvate. Likewise, non-coordinated solvent is used herein as term for physisorbed or physically entrapped solvent (definitions according to Polymorphism in the Pharmaceutical Industry (Ed. R. Hilfiker, V C H, 2006), Chapter 8: U. J. Griesser: The Importance of Solvates). Crystalline form 1 in particular comprises no coordinated or non-coordinated solvent/water.

2) Another embodiment relates to a crystalline form of COMPOUND according to embodiment 1); characterized by the presence of peaks in the X-ray powder diffraction diagram at the following angles of refraction 2θ: 5.6° 12.4°, 14.8°, 17.7°, and 21.5°.

3) Another embodiment relates to a crystalline form of COMPOUND according to embodiment 1); characterized by the presence of peaks in the X-ray powder diffraction diagram at the following angles of refraction 2θ: 5.6° 12.4°, 13.4°, 14.8°, 16.8°, 17.7°, 19.4°, 21.5°, 22.1°, and 24.2°.

4) Another embodiment relates to a crystalline form of COMPOUND according to embodiment 1), which essentially shows the X-ray powder diffraction pattern as depicted in FIG. 1.

For avoidance of any doubt, whenever one of the above embodiments refers to "peaks in the X-ray powder diffraction diagram at the following angles of refraction 2θ", said X-ray powder diffraction diagram is obtained by using combined Cu Kα1 and Kα2 radiation, without Kα2 stripping; and it should be understood that the accuracy of the 2θ values as provided herein is in the range of +/−0.1-0.2°. Notably, when specifying an angle of refraction 2theta (2θ) for a peak in the invention embodiments and the claims, the 2θ value given is to be understood as an interval from said value minus 0.2° to said value plus 0.2° (2θ+/−0.2°); and preferably from said value minus 0.1° to said value plus 0.1° (2θ+/−0.1°).

5) Another embodiment relates to a crystalline form of COMPOUND according to any one of embodiments 1) to 4); which shows endothermal melting with a peak at about 130° C. as determined by differential scanning calorimetry (e.g. by using the method as described herein).

6) Another embodiment relates to a crystalline form of COMPOUND according to any one of embodiments 1) to 5), wherein said crystalline form consists essentially of particles having a particle size distribution, wherein D50 is equal or greater than 50 μm (notably is equal or greater than 60 μm; especially is equal or greater than 70 μm). A subembodiment relates to a crystalline form of COMPOUND according to any one of embodiments 1) to 5), wherein said crystalline form consists essentially of particles having a particle size distribution, wherein D50 is from about 50 μm to about 300 μm (notably from about 60 μm to about 280 μm; especially from about 70 μm to about 250 μm).

7) Another embodiment relates to a crystalline form of COMPOUND according to any one of embodiments 1) to 5), wherein said crystalline form consists essentially of particles having a particle size distribution, wherein D50 is from about 50 μm to about 120 μm (notably from about 60 μm to about 120 μm; especially from about 70 μm to about 120 μm).

8) Another embodiment relates to a crystalline form of COMPOUND according to any one of embodiments 1) to 5), wherein said crystalline form consists essentially of particles having a particle size distribution, wherein D50 is from about 50 μm to about 150 μm (notably from about 70 μm to about 150 μm, especially from about 80 μm to about 150 μm, in particular from about 100 μm to 150 μm);

9) Another embodiment relates to a crystalline form of COMPOUND according to any one of embodiments 1) to 8), wherein said crystalline form consists essentially of particles having a particle size distribution, wherein D10 is from about 3 μm to about 12 μm (especially from about 4 μm to about 10 μm).

10) Another embodiment relates to a crystalline form of COMPOUND according to any one of embodiments 1) to 9), wherein said crystalline form consists essentially of particles having a particle size distribution, wherein D90 is from about 100 μm to about 400 μm (notably from about 150 μm to about 350 μm, especially from about 200 μm to about 350 μm).

11) Another embodiment relates to a crystalline form of COMPOUND according to any one of embodiments 1) to 5), wherein said crystalline form consists essentially of particles having a particle size distribution, wherein D50 is from about 50 μm to about 120 μm (notably from about 60 μm to about 120 μm; especially from about 70 μm to about 120 μm); and D90 is from about 100 μm to about 400 μm (notably from about 150 μm to about 350 μm, especially from about 200 μm to about 350 μm);

and preferably D10 is from about 3 μm to about 12 μm (especially from about 4 μm to about 10 μm).

12) Another embodiment relates to a crystalline form of COMPOUND according to any one of embodiments 1) to 5), wherein said crystalline form consists essentially of particles having a particle size distribution, wherein D50 is from about 50 μm to about 150 μm (notably from about 70 μm to about 150 μm, especially from about 80 μm to about 150 μm, in particular from about 100 μm to about 150 μm); and D90 is from about 100 μm to about 400 μm (notably from about 150 μm to about 350 μm, especially from about 200 μm to about 350 μm);

and preferably D10 is from about 3 μm to about 12 μm (especially from about 4 μm to about 10 μm).

Particle size distributions are defined herein as D10, D50 and D90. D10, D50 and D90 represent the particle diameter corresponding to the respective percentage in volume (i.e. 10%, 50%, 90%) of a given sample which is below the indicated diameter. For example, a D50 from about 70 μm to about 150 μm means that 50% of the volume of a given sample has a diameter which is equal or below a diameter that is in the range between about 70 μm and about 150 μm. Particle size distributions may be determined using standard procedures such as laser diffraction.

13) Another embodiment relates to a crystalline form of COMPOUND according to any one of embodiments 1) to 12), wherein said crystalline form has a total impurity amount less than about 0.5%, notably less than about 0.4%.

The total impurity amount as expressed herein may be determined by HPLC and represents a ratio of the amount of essentially all detectable impurities divided by the sum of the amount of essentially all detectable impurities and the amount of COMPOUND, expressed in percent. Said amounts of essentially all detectable impurities and the amount of COMPOUND may be determined by an HPLC method (especially by the HPLC method described herein). Notably, said amounts can be determined by using the area under the curve of the elution peaks of essentially all detectable impurities and COMPOUND. The term "essentially all detectable impurities" means essentially all impurities which can be detected using the HPLC method described herein.

The amount of impurities may for example be determined by standard HPLC performed on Dionex, Acclaim Polar Advantage 2 C18 250×3 mm 3 μm 120A using a mixture of eluent A (Buffer/CH3CN=100/2) and eluent B (Buffer/CH3CN=70/30), wherein Buffer is 8 mM ammonium acetate buffer with a pH of 8.5, with the following gradient (Time [min]-A [%]-B [%]): 0-100-0; 2-93-7; 5.5-50-50; 9-50-50; 10-100-0; 18-100-0; at column temperature of 25° C. Flow rate may be 0.5 ml/min and detection may be performed at 215 nm with a bandwidth of 4 nm. Sample of COMPOUND (2 mg/ml) may be prepared in eluent A before injecting 20 μl thereof into an HPLC system.

Table 1 below summarizes typical retention times of some impurities and COMPOUND.

TABLE 1

| Chemical name | $t_R$ [min] |
|---|---|
| (2S,3R,4R,5S)-1-butyl-2-(hydroxymethyl)piperidine-3,4,5-triol | 10.1 |
| (2R,3S,4R,5S)-1-butyl-2-(hydroxymethyl)piperidine-3,4,5-triol (COMPOUND) | 10.6 |
| (2S,3S,4R,5S)-1-butyl-2-(hydroxymethyl)piperidine-3,4,5-triol | 11.2 |
| (2R,3S,4R,5R)-1-butyl-2-(hydroxymethyl)-piperidine-3,4,5-triol (main impurity) | 11.4 |

14) Another embodiment relates to a crystalline form of COMPOUND according to any one of embodiments 1) to 13), wherein said crystalline form contains less than 0.5%, notably less than 0.4%, especially less than 0.3% of (2R,3S,4R,5R)-1-butyl-2-(hydroxymethyl)-piperidine-3,4,5-triol.

The amount of (2R,3S,4R,5R)-1-butyl-2-(hydroxymethyl)-piperidine-3,4,5-triol as defined herein may be determined by HPLC (for example by the HPLC method described herein) and represents a ratio of the amount of (2R,3S,4R,5R)-1-butyl-2-(hydroxymethyl)-piperidine-3,4,5-triol as determined by the area under the curve of the elution peak of said compound divided by the sum of the amount of essentially all detectable impurities and the amount of COMPOUND, determined by the area under the curve of their elution peaks, expressed in percent.

15) A process for the preparation of crystalline form of COMPOUND according to any one of embodiments 1) to 14), wherein said process comprises:

i. Preparing a solution of COMPOUND in methanol, wherein preferably about 50 ww % to 85 ww % of methanol with respect to the weight of COMPOUND is used (especially about 65 ww % to 80 ww %, in particular about 70 ww % to 80 ww %);

ii. Adding water and acetone to said solution, wherein preferably about 10 ww % to 35 ww % of water with respect to the weight of COMPOUND is used (especially about 15 ww % to 30 ww %, in particular about 20 ww % to 25 ww %); and wherein preferably about 250 ww % to 500 ww % of acetone with respect to the weight of COMPOUND is used (especially about 250 ww % to 400 ww %, in particular about 300 ww % to 400 ww %);

iii. Warming up the mixture to about 45° C. to 60° C. (especially about 50° C. to 57° C., in particular about 55° C.);

iv. Adding further acetone to the mixture obtained in step c), wherein preferably about 400 ww % to 700 ww % of acetone with respect to the weight of COMPOUND is used (especially about 450 ww % to 650 ww %, in particular about 500 ww % to 600 ww %); wherein in step d) preferably the temperature of step c) is maintained; and wherein preferably the acetone is added at said temperature during at least about 1 hour (especially during about 2 hours);

v. Optionally cooling the mixture to a temperature of about 35° C. to 45° C. (especially about 40° C.) during about 1 hour, and stirring at this temperature until crystals appear; and/or optionally adding seed crystals;

vi. Cooling the mixture to about −10° C. to 5° C. (especially to about −5° C. to 0° C.), wherein said cooling step is preferably effected during about 1 to 4 hours (especially during about 1 to 3 hours, in particular about 2 hours);

vii. Agitating (for example stirring) at the final temperature of step f) for at least about 0.5 hour (especially for about 2 hours);

viii. Isolating the product by solid-liquid separation (such as especially filtering);

ix. Washing the solid with acetone (especially about three times at a temperature of about 0° C. to 10° C., in particular at about 5° C., wherein preferably about 150 ww % to 300 ww % of acetone with respect to the weight of COMPOUND is used); and x. Drying (using usual conditions such as air flow or preferably drying under vacuum conditions at a temperature of about 20° C. to 50° C. for at least 5 hours (especially at about 40° C. for at least about 10 hours).

16) A process for the preparation of crystalline form of COMPOUND according to any one of embodiments 1) to 14), wherein said process comprises:

I) Step 1 comprising:

i. Preparing a solution of COMPOUND in isopropanol, wherein preferably about 100 ww % to 140 ww % of isopropanol with respect to the weight of COMPOUND is used (especially about 110 ww % to 130 ww %, in particular about 120 ww %);

ii. Warming up the solution to about 45° C. to 60° C. (especially about 50° C. to 56° C., in particular about 55° C.);

xi. Adding anhydrous acetone, wherein about 450 ww % to 550 ww % with respect to the weight of COMPOUND is added (especially about 470 ww % to 530 ww %; notably about 500 ww %), and wherein said acetone is added during about 30 min;

iii. Cooling the obtained solution to about −5° C. to +5° C. (especially to about 0° C.) at a constant rate (especially at a rate of about 0.27° C./min);

iv. Agitating (for example stirring) at about 0° C. for 1 to 3 hours (especially for 2 hour);

v. Isolating the product by solid-liquid separation (such as especially filtering);

vi. Washing the solid with anhydrous acetone (especially at temperature of about 0° C.), wherein about 250 ww % to 300 ww % of acetone with respect to the weight of COMPOUND (especially about 270 ww %) is used; and vii. Drying (using usual conditions such as air flow or preferably drying under vacuum conditions (especially at about 30° C. for at least about 18 hours)).

II) Step 2 comprising:

i. Dissolving the product of the first crystallization step at about 45° C. in about 200 ww % to 250 ww % (especially about 225 ww %) methanol with respect to the weight of COMPOUND;

ii. Filtering over activated carbon (especially over about 9 ww % of activated carbon with respect to the weight of COMPOUND);

iii. Washing the activated carbon with about 90 ww % of methanol with respect to the weight of COMPOUND;

iv. Concentrating the solution under vacuum (especially at temperature about 45° C.) (notably until no further distillate is observed);

v. Dissolving the distillation residue of the previous step in about 60 ww % to 65 ww % methanol and about 4 ww % to 8 ww % water (especially in about 63 ww % methanol and about 6 ww % water) with respect to the weight of COMPOUND;

vi. Warming up the solution to about 55° C. to 58° C. (especially about 56° C.).

vii. Adding about 200 ww % to 220 ww % (especially about 210 ww %) ethyl acetate during about 25 min to 45 min (especially about 30 min) while keeping the temperature between about 55° C. to 58° C.;

viii. Cooling the resulting suspension down to about −5 to +5° C. (especially to about 0° C.) at a constant rate (especially at a constant rate of about 0.9° C./min).

ix. Agitating (for example stirring) at about 0° C. for 1.5 to 3 hours (especially for 2 hour);

x. Isolating the product by solid-liquid separation (such as especially filtering);

xi. Washing the solid twice with ethyl acetate (especially at temperature of about 0° C.); wherein especially about 35 ww % to 55 ww % of ethyl acetate with respect to the weight of COMPOUND is used; and xii. Drying (using usual conditions such as air flow or preferably drying under vacuum conditions (especially at about 30° C. for at least about 20 hours)).

Activated carbon as used in the process of embodiment 16) may be a steam activated carbon such as Norit™ SX1.

17) Another embodiment the present invention relates to a crystalline form of COMPOUND according to any one of embodiments 1) to 12), obtainable by the process according to embodiment 15); or to a crystalline form of COMPOUND according to any one of embodiments 1) to 14), obtainable by the process according to embodiment 16).

18) A further embodiment of the invention relates to a pharmaceutical composition comprising as active ingredient a crystalline form of COMPOUND according to any one of embodiments 1) to 14) and 17), and at least one pharmaceutically acceptable carrier material.

19) A further embodiment of the invention relates to a pharmaceutical composition comprising:

from about 55 ww % to about 75 ww % of crystalline COMPOUND according to any one of embodiments 1) to 14) and 17), (especially from about 55 ww % to about 65 ww % of said crystalline COMPOUND); and from about 25 ww % to about 45 ww % of one or more diluents selected from a group consisting of lactose anhydrous, silicified mycrocristalinne cellulose, microcrystalline cellulose, calcium hydrogen phosphate and isomalt (notably lactose anhydrous) (especially from about 35 ww % to about 45 ww % of lactose anhydrous).

20) A further embodiment of the invention relates to a pharmaceutical composition comprising:

from about 55 ww % to about 75 ww % of crystalline COMPOUND according to any one of embodiments 1) to 14) and 17) (especially from about 55 ww % to about 65 ww % of said crystalline COMPOUND);

from about 24 ww % to about 44 ww % of one or more diluents selected from a group consisting of lactose anhydrous, silicified mycrocristalinne cellulose, microcrystalline cellulose, calcium hydrogen phosphate and isomalt (notably lactose anhydrous) (especially from about 34 ww % to about 44 ww % of lactose anhydrous); and from 0 ww % to about 6 ww % of a component selected from a group consisting of talc, magnesium sterate, sodium sterayl fumarate, silicon dioxide, or a combination thereof.

21) A further embodiment of the invention relates to a pharmaceutical composition comprising:

from about 55 ww % to about 75 ww % of crystalline COMPOUND according to any one of embodiments 1) to 14) and 17) (especially from about 55 ww % to about 65 ww % of said crystalline COMPOUND);

from about 24 ww % to about 44 ww % of a diluent which is lactose (especially from about 34 ww % to about 44 ww % of lactose anhydrous, in particular of commercial SuperTab® 21AN of DFE Pharma);

from 0 ww % to about 6 ww % of talc; and from 0 ww % to about 6 ww % of silicon dioxide.

22) A further embodiment of the invention relates to a pharmaceutical composition consisting essentially of:

from about 55 ww % to about 75 ww % of crystalline COMPOUND according to any one of embodiments 1) to 14) and 17) (especially from about 55 ww % to about 65 ww % of said crystalline COMPOUND);

from about 24 ww % to about 44 ww % of a diluent which is lactose (especially from about 34 ww % to about 44 ww % of lactose anhydrous, in particular of commercial SuperTab® 21AN of DFE Pharma);

from 0 ww % to about 6 ww % of talc; and from 0 ww % to about 6 ww % of silicon dioxide.

It is understood the total ww % of the pharmaceutical composition of embodiment 22) is 100.

23) A further embodiment of the invention relates to a pharmaceutical composition according to any one of embodiments 18) to 22), wherein the tapped density of said pharmaceutical composition is at least 0.64 g/mL.

The tapped density of solid pharmaceutical compositions such as powders, blends, etc. can be measured in accordance with USP Chapter <616> Method 2 and Ph.Eur. Chapter 2.9.34.

The excipient lactose as used herein refers to commercially available pharmaceutical grade lactose (4-O-β-D-galactopyranosyl-D-glucose; CAS Reg. No 63-42-3).

Lactose anhydrous as used in the compositions of embodiments 18) to 22) above preferably is anhydrous lactose characterized in that from 0 ww % to about 20 ww % of all particles have a particle size of less than 45 μm; from about 40 ww % to about 65 ww % of all particles have a particle size of less than 150 μm; and from about 80 ww % to about 100 ww % of all particles have a particle size of less than 250 μm, wherein the particle size is determined in accordance with a standard procedure ISO 4610. In particular, anhydrous commercial lactose SuperTab® 21AN of DFE Pharma may be used.

24) A further embodiment relates to the pharmaceutical composition according to any one of embodiments 18) to 23), said composition comprising one or more diluents (notably one diluent which is lactose; especially lactose anhydrous), wherein the one or more diluents (notably the lactose; especially the lactose anhydrous) has/have a particle size characterized in that from 0 ww % to about 20 ww % of all particle s have a particle size of less than 45 μm; from about 40 ww % to about 65 ww % of all particles have a particle size of less than 150 μm; and from about 80 ww % to about 100 ww % of all particles have a particle size of less than 250 μm (notably, wherein the particle size is determined in accordance with a standard procedure ISO 4610).

25) A capsule (especially a hard gelatine capsule) comprising the pharmaceutical composition according to any one of embodiments 18) to 24), wherein notably such capsule comprises COMPOUND according to any one of embodiments 1) to 14) and 17) in an amount of about 250 mg of active ingredient per capsule; wherein especially such capsule is a size 0 capsule, in particular a size 0 hard gelatine capsule.

Any type of capsule that is usually used to contain pharmaceutical compositions in the form of powder or pellets such as hard gelatine capsules, HPMC capsules, etc. may be used in the present invention.

Where the plural form is used for compounds, solid, pharmaceutical compositions, diseases and the like, this is intended to mean also a single compound, solid, or the like.

The term "consisting essentially of" is understood in the context of the present invention to mean especially that the respective composition consists in an amount of at least 90, notably of at least 95, especially of at least 99, and preferably in an amount of 100 percent by weight (i.e. in the meaning of "consisting of") of the respective composition in the amounts as explicitly stated in the respective embodiment. The term "comprising" is preferably to be understood in the meaning of the term "consisting essentially of".

The term "essentially", for example when used in a term such as "essentially pure" is understood in the context of the present invention to mean especially that the respective composition/compound etc. consists in an amount of at least 90, especially of at least 95, and notably of at least 99 percent by weight of the respective pure composition/compound/crystalline form etc.

The term "enantiomerically enriched" is understood in the context of the present invention to mean especially that at least 90, preferably at least 95, and most preferably at least 99 percent by weight of the COMPOUND are present in form of one enantiomer of the COMPOUND. It is understood that COMPOUND is present in enantiomerically enriched absolute (2R,3S,4R,5S)-configuration.

When defining the presence of a peak in e.g. an X-ray powder diffraction diagram, a common approach is to do this in terms of the S/N ratio (S=signal, N=noise). According to this definition, when stating that a peak has to be present in an X-ray powder diffraction diagram, it is understood that the peak in the X-ray powder diffraction diagram is defined by having an S/N ratio (S=signal, N=noise) of greater than x (x being a numerical value greater than 1), usually greater than 2, especially greater than 3.

In the context with stating that the crystalline form essentially shows an X-ray powder diffraction pattern as depicted in FIG. 1, respectively, the term "essentially" means that at least the major peaks of the diagram depicted in said figures, i.e. those having a relative intensity of more than 10%, especially more than 20%, as compared to the most intense peak in the diagram, have to be present. However, the person skilled in the art of X-ray powder diffraction will recognize that relative intensities in X-ray powder diffraction diagrams may be subject to strong intensity variations due to preferred orientation effects.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., preferably to an interval extending from Y minus 5° C. to Y plus 5° C., notably to an interval extending from Y minus 3° C. to Y plus 3° C. Room temperature means a temperature of about 25° C. When in the current application the term n equivalent(s) is used wherein n is a number, it is meant and within the scope of the current application that n is referring to about the number n, preferably n is referring to the exact number n.

Whenever the word "between" or "to" is used to describe a numerical range, it is to be understood that the end points of the indicated range are explicitly included in the range. For example: if a temperature range is described to be between 40° C. and 80° C. (or 40° C. to 80° C.), this means that the end points 40° C. and 80° C. are included in the range; or if a variable is defined as being an integer between 1 and 4 (or from 1 to 4), this means that the variable is the integer 1, 2, 3, or 4.

The expression "ww %" (or % (w/w)) refers to a percentage by weight compared to the total weight of the composition considered. If not explicitly stated otherwise, the considered total weight is the total weight of the pharmaceutical composition.

It is understood that the total amount expressed in "ww %" of a certain composition is 100.

The expression (wt/wt) relating to a ratio refers to a ratio by weight of the respective components.

In case a certain value is given as % value, in absence of further specification such value refers to ww %, or if in the context of purity, area % as measured by HPLC.

Likewise, the expression v/v refers to a ratio by volume of the two components considered. The expression "vol" signifies volumes (in L, e.g. of solvent) per weight (in kg, e.g. of reactant). For example, 7 vol signifies 7 liters (of solvent) per kg (of reactant).

The term "solid-liquid separation" refers to routine solid-liquid separation techniques well known to a skilled person (see for example Perry's Chemical Engineers' Handbook, 7th edition, Perry, R. H.; Green, D. W. McGraw-Hill 1997). In particular, the term includes techniques such as filtration, centrifugation, and gravity sedimentation; especially filtration.

The crystalline forms, especially the essentially pure crystalline forms, of COMPOUND according to any one of embodiments 1) to 14) and 17) and the compositions according to any one of embodiments 18) to 24) can be used as medicaments, e.g. in the form of pharmaceutical compositions for enteral or parenteral administration. Further, the capsule according to embodiment 25) can be used as a medicament, e.g. in the form of pharmaceutical composition for enteral administration.

Another embodiment thus relates to a crystalline form of COMPOUND according to any one of embodiments 1) to 14) and 17), the compositions according to any one of embodiments 18) to 24) or the capsule according to embodiment 25) for use as a medicament.

The crystalline solid, especially the essentially pure crystalline solid, of COMPOUND according to any one of embodiments 1) to 14) and 17) may be used as single component or as mixtures with other crystalline forms and/or the amorphous form of COMPOUND.

For avoidance of any doubt, it is well understood that the pharmaceutical composition as defined in any one of embodiments 18) to 21) may additionally comprise further conventional excipients and/or additives, which may be used alone or in combination (quantum satis, i.e. wherein the maximum amounts of said further conventional ingredients and/or additives may need to be reduced to make up the total ww % of 100).

Reference is made to the extensive literature on the subject for these and other pharmaceutically acceptable excipients and procedures mentioned herein, see for example R. C. Rowe, P. J. Seskey, S. C. Owen, Handbook of Pharmaceutical Excipients, 5th edition, Pharmaceutical Press 2006; Remington, *The Science and Practice of Pharmacy*, 21st Edition (2005), Part 5, "Pharmaceutical Manufacturing" [published by Lippincott Williams & Wilkins].

The total ww % of the pharmaceutical composition as defined in any one of embodiments 18) to 24) is 100.

The term "pharmaceutical composition" is interchangeable with the terms "formulation", or "composition".

A composition is considered physically "stable", if during a certain period of time variations of less than 30%, preferably less than 20% and most preferably less than 10% with regard to residual moisture are observed. Additionally, the appearance may be considered as criterion to determine physical stability of a composition.

A pharmaceutical composition is considered chemically "stable", if under certain conditions and during a certain period of time at least 80%, notably at least 95%, especially at least 98%, and preferably at least 99% of the initial content of COMPOUND is maintained under said conditions and over said period of time without degradation.

Preferably, the pharmaceutical compositions of this invention will be chemically and physically "stable" for at least 6, preferably for at least 12 months when kept at a temperature of 5° C. to 50° C. and a rH of about 75% or below. More preferably, they will be stable for at least 6 or preferably for 12 months when kept at a temperature of 15° C. to 45° C. and a rH of about 75% or below. Most preferred, they will be stable for at least 6 or preferably for 12 months when kept at a temperature of 25° C. to 40° C. and a rH of about 75% or below, especially at 40° C. and 75% rH, or in particular at 25° C. and 60% rH.

The chemical stability of the pharmaceutical compositions may be tested in conventional manner, e.g. by measurement of the COMPOUND and its degradation products. The content of COMPOUND and its degradation products may be evaluated via conventional HPLC.

The physical stability of the pharmaceutical compositions may be tested in conventional manner, e.g. by measurement of water content; and/or appearance of the composition, e.g. after storage at a certain temperature and relative humidity for defined periods of time.

26) A further embodiment of the invention relates to a crystalline form of COMPOUND according to any one of embodiments 1) to 14) and 17) for use in the manufacture of a pharmaceutical composition, especially for use in the manufacture of a pharmaceutical composition according to any one of embodiments 18) to 24) and especially for use in the manufacture of a capsule according to embodiment 25).

For avoidance of any doubt, aspects of embodiment 26) refer to the COMPOUND in crystalline form according to any one of embodiments 1) to 14) and 17), which is suitable for the manufacture of a pharmaceutical composition/which is used as final isolation step of COMPOUND (e.g. in order to meet the purity requirements of pharmaceutical production), whereas the final pharmaceutical composition according to any one of embodiments 18) to 24) may or may not contain said crystalline form (e.g. because the originally crystalline form of COMPOUND is further transformed during the manufacturing process and/or is dissolved in the pharmaceutically acceptable carrier material(s); thus, in the final pharmaceutical composition, COMPOUND may be present in non-crystalline form, in another crystalline form, or in dissolved form, or the like).

Such crystalline COMPOUND according to embodiments 1) to 14) and 17), or such pharmaceutical compositions according to any one of embodiments 18) to 24), or a capsule according to embodiment 25) are especially useful for the prevention/prophylaxis or treatment of glycolipid storage diseases or related disorders such as especially Niemann-Pick type C disease, Gaucher disease types 1, 2 and 3, GM2 gangliosidoses (including Tay-Sachs disease, Sandhoff disease, GM2 gangliosidosis AB variant), GM1 gangliosidosis, Fabry disease, Schindler disease, Smith-Lemly-Opitz syndrome, Tangier disease, mucolipidosis IV, mucopolysaccharidoses, GbA1-synucleopathies and syndromes thereof, Huntington's disease, polycystic kidney disease, Darier's disease, and Guillain-Barré syndrome; as well as the inflammatory components of human malignancies; infectious diseases such as urinary tract infection; neuronal disorders and neurodegenerative processes such as Alzheimer's disease, epilepsy, Parkinson's disease and syndromes thereof, stroke, spinal cord injuries, motor neuron disease (ALS), multiple sclerosis, and Lewy-Body dementia; inflammatory diseases and other disorders associated with macrophage recruitment and activation, including rheumatoid arthritis, Crohn's disease, asthma and sepsis; Krabbe disease; and cystic fibrosis.

27) A further embodiment of the invention relates to a crystalline form of COMPOUND according to any one of embodiments 1) to 14) and 17), or to a pharmaceutical composition according to any one of embodiments 18) to 24), or to a capsule according to embodiment 25) for use as glycolipid biosynthesis inhibitor in a substrate reduction method for reducing the amount of glycolipids in a patient having a glycolipid storage disease or related disorder.

28) A further embodiment of the invention relates to a crystalline form of COMPOUND according to any one of embodiments 1) to 14) and 17), or to a pharmaceutical composition according to any one of embodiments 18) to 24), or to a capsule according to embodiment 25) for use in the prevention/prophylaxis or treatment of Niemann-Pick type C disease; Gaucher disease types 1, 2 and 3; GM2 gangliosidoses (including Tay-Sachs disease, Sandhoff disease, GM2 gangliosidosis AB variant); GM1 gangliosidosis; Fabry disease; Schindler disease; Smith-Lemly-Opitz syndrome; Tangier disease; mucolipidosis IV; mucopolysaccharidoses; GbA1-synucleopathies and syndromes thereof; Huntington's disease; polycystic kidney disease; Darier's disease; Guillain-Barré syndrome; the inflammatory components of human malignancies; infectious diseases such as urinary tract infection; neuronal disorders and neurodegenerative processes such as Alzheimer's disease, epilepsy, Parkinson's disease and syndromes thereof, stroke, spinal cord injuries, motor neuron disease (ALS), multiple sclerosis, and Lewy-Body dementia; inflammatory diseases and other disorders associated with macrophage recruitment and activation including rheumatoid arthritis, Crohn's disease, asthma and sepsis; Krabbe disease; or cystic fibrosis.

29) A further embodiment of the invention relates to a crystalline form of COMPOUND according to any one of embodiments 1) to 14) and 17), or to a pharmaceutical composition according to any one of embodiments 18) to 24), or to a capsule according to embodiment 25) for use in the prevention/prophylaxis or treatment of Niemann-Pick type C disease; Gaucher disease types 1, 2 and 3; GM2 gangliosidoses (including Tay-Sachs disease, Sandhoff disease, GM2 gangliosidosis AB variant); GM1 gangliosidosis; Fabry disease; Schindler disease; Smith-Lemly-Opitz syndrome; Tangier disease; mucolipidosis IV; mucopolysaccharidoses; GbA1-synucleopathies and syndromes thereof; Huntington's disease; polycystic kidney disease; Darier's disease; or Guillain-Barré syndrome.

30) A further embodiment of the invention relates to a crystalline form of COMPOUND according to any one of embodiments 1) to 14) and 17), or to a pharmaceutical composition according to any one of embodiments 18) to 24), or to a capsule according to embodiment 25) for use in the prevention/prophylaxis or treatment of Fabry disease.

For avoidance of any doubt, if compounds are described as useful for the prevention or treatment of certain diseases, such compounds are likewise suitable for use in the preparation of a medicament for the prevention or treatment of said diseases.

The term "prevent" or "prevention" or "preventing" used with reference to a disease means either that said disease does not occur in the patient or animal, or that, although the animal or patient is affected by the disease, part or all the symptoms of the disease are either reduced or absent.

The term "treat" or "treatment" or "treating" used with reference to a disease means either that said disease is cured in the patient or animal, or that, although the animal or patient remains affected by the disease, part or all the symptoms of the disease are either reduced or eliminated.

The terms "prevent", "prevention" or "preventing" may be understood to mean "prophylaxis".

The present invention also relates to a method for the prevention/prophylaxis or treatment of a disease or disorder mentioned herein comprising administering to a subject (notably a mammal, especially a human) a pharmaceutically active amount of the COMPOUND in crystalline form according to any one of embodiments 1) to 14) and 17), or comprising administering to a subject a pharmaceutical composition according to any one of embodiments 18) to 24), or comprising administering to a subject a capsule according to embodiment 25).

The present invention also relates to a process for the preparation of COMPOUND in crystalline and enantiomerically enriched form, and to processes for the preparation and characterization of the crystalline forms of COMPOUND according to any one of embodiments 1) to 14) and 17). Said processes are described in embodiments 15) and 16), as well as in the procedures of the experimental part below.

Based on the dependencies of the different embodiments 1) to 30) as disclosed hereinabove, the following embodiments are thus possible and intended and herewith specifically disclosed in individualized form:

1, 2+1, 3+1, 5+1, 5+2+1, 5+3+1, 6+1, 6+2+1, 6+3+1, 6+5+1, 6+5+2+1, 6+5+3+1, 7+1, 7+2+1, 7+3+1, 7+5+1, 7+5+2+1, 7+5+3+1, 8+1, 8+2+1, 8+3+1, 8+5+1, 8+5+2+1, 8+5+3+1, 9+1, 9+2+1, 9+3+1, 9+5+1, 9+5+2+1, 9+5+3+1, 9+6+1, 9+6+2+1, 9+6+3+1, 9+6+5+1, 9+6+5+2+1, 9+6+5+3+1, 9+7+1, 9+7+2+1, 9+7+3+1, 9+7+5+1, 9+7+5+2+1, 9+7+5+3+1, 9+8+1, 9+8+2+1, 9+8+3+1, 9+8+5+1, 9+8+5+2+1, 9+8+5+3+1, 10+1, 10+2+1, 10+3+1, 10+5+1, 10+5+2+1, 10+5+3+1, 10+6+1, 10+6+2+1, 10+6+3+1, 10+6+5+1, 10+6+5+2+1, 10+6+5+3+1, 10+7+1, 10+7+2+1, 10+7+3+1, 10+7+5+1, 10+7+5+2+1, 10+7+5+3+1, 10+8+1, 10+8+2+1, 10+8+3+1, 10+8+5+1, 10+8+5+2+1, 10+8+5+3+1, 10+9+1, 10+9+2+1, 10+9+3+1, 10+9+5+1, 10+9+5+2+1, 10+9+5+3+1, 10+9+6+1, 10+9+6+2+1, 10+9+6+3+1, 10+9+6+5+1, 10+9+6+5+2+1, 10+9+6+5+3+1, 10+9+7+1, 10+9+7+2+1, 10+9+7+3+1, 10+9+7+5+1, 10+9+7+5+2+1, 10+9+7+5+3+1, 10+9+8+1, 10+9+8+2+1, 10+9+8+3+1, 10+9+8+5+1, 10+9+8+5+2+1, 10+9+8+5+3+1, 11+1, 11+2+1, 11+3+1, 11+5+1, 11+5+2+1, 11+5+3+1, 12+1, 12+2+1, 12+3+1,

12+5+1, 12+5+2+1, 12+5+3+1, 13+1, 13+2+1, 13+3+1, 13+5+1, 13+5+2+1, 13+5+3+1, 13+6+1, 13+6+2+1, 13+6+3+1, 13+6+5+1, 13+6+5+2+1, 13+6+5+3+1, 13+7+1, 13+7+2+1, 13+7+3+1, 13+7+5+1, 13+7+5+2+1, 13+7+5+3+1, 13+8+1, 13+8+2+1, 13+8+3+1, 13+8+5+1, 13+8+5+2+1, 13+8+5+3+1, 13+9+1, 13+9+2+1, 13+9+3+1, 13+9+5+1, 13+9+5+2+1, 13+9+5+3+1, 13+9+6+1, 13+9+6+2+1, 13+9+6+3+1, 13+9+6+5+1, 13+9+6+5+2+1, 13+9+6+5+3+1, 13+9+7+1, 13+9+7+2+1, 13+9+7+3+1, 13+9+7+5+1, 13+9+7+5+2+1, 13+9+7+5+3+1, 13+9+8+1, 13+9+8+2+1, 13+9+8+3+1, 13+9+8+5+1, 13+9+8+5+2+1, 13+9+8+5+3+1, 13+10+1, 13+10+2+1, 13+10+3+1, 13+10+5+1, 13+10+5+2+1, 13+10+5+3+1, 13+10+6+1, 13+10+6+2+1, 13+10+6+3+1, 13+10+6+5+1, 13+10+6+5+2+1, 13+10+6+5+3+1, 13+10+7+1, 13+10+7+2+1, 13+10+7+3+1, 13+10+7+5+1, 13+10+7+5+2+1, 13+10+7+5+3+1, 13+10+8+1, 13+10+8+2+1, 13+10+8+3+1, 13+10+8+5+1, 13+10+8+5+2+1, 13+10+8+5+3+1, 13+10+9+1, 13+10+9+2+1, 13+10+9+3+1, 13+10+9+5+1, 13+10+9+5+2+1, 13+10+9+5+3+1, 13+10+9+6+1, 13+10+9+6+2+1, 13+10+9+6+3+1, 13+10+9+6+5+1, 13+10+9+6+5+2+1, 13+10+9+6+5+3+1, 13+10+9+7+1, 13+10+9+7+2+1, 13+10+9+7+3+1, 13+10+9+7+5+1, 13+10+9+7+5+2+1, 13+10+9+7+5+3+1, 13+10+9+8+1, 13+10+9+8+2+1, 13+10+9+8+3+1, 13+10+9+8+5+1, 13+10+9+8+5+2+1, 13+10+9+8+5+3+1, 13+11+1, 13+11+2+1, 13+11+3+1, 13+11+5+1, 13+11+5+2+1, 13+11+5+3+1, 13+12+1, 13+12+2+1, 13+12+3+1, 13+12+5+1, 13+12+5+2+1, 13+12+5+3+1, 14+1, 14+2+1, 14+3+1, 14+5+1, 14+5+2+1, 14+5+3+1, 14+6+1, 14+6+2+1, 14+6+3+1, 14+6+5+1, 14+6+5+2+1, 14+6+5+3+1, 14+7+1, 14+7+2+1, 14+7+3+1, 14+7+5+1, 14+7+5+2+1, 14+7+5+3+1, 14+8+1, 14+8+2+1, 14+8+3+1, 14+8+5+1, 14+8+5+2+1, 14+8+5+3+1, 14+9+1, 14+9+2+1, 14+9+3+1, 14+9+5+1, 14+9+5+2+1, 14+9+5+3+1, 14+9+6+1, 14+9+6+2+1, 14+9+6+3+1, 14+9+6+5+1, 14+9+6+5+2+1, 14+9+6+5+3+1, 14+9+7+1, 14+9+7+2+1, 14+9+7+3+1, 14+9+7+5+1, 14+9+7+5+2+1, 14+9+7+5+3+1, 14+9+8+1, 14+9+8+2+1, 14+9+8+3+1, 14+9+8+5+1, 14+9+8+5+2+1, 14+9+8+5+3+1, 14+10+1, 14+10+2+1, 14+10+3+1, 14+10+5+1, 14+10+5+2+1, 14+10+5+3+1, 14+10+6+1, 14+10+6+2+1, 14+10+6+3+1, 14+10+6+5+1, 14+10+6+5+2+1, 14+10+6+5+3+1, 14+10+7+1, 14+10+7+2+1, 14+10+7+3+1, 14+10+7+5+1, 14+10+7+5+2+1, 14+10+7+5+3+1, 14+10+8+1, 14+10+8+2+1, 14+10+8+3+1, 14+10+8+5+1, 14+10+8+5+2+1, 14+10+8+5+3+1, 14+10+9+1, 14+10+9+2+1, 14+10+9+3+1, 14+10+9+5+1, 14+10+9+5+2+1, 14+10+9+5+3+1, 14+10+9+6+1, 14+10+9+6+2+1, 14+10+9+6+3+1, 14+10+9+6+5+1, 14+10+9+6+5+2+1, 14+10+9+6+5+3+1, 14+10+9+7+1, 14+10+9+7+2+1, 14+10+9+7+3+1, 14+10+9+7+5+1, 14+10+9+7+5+2+1, 14+10+9+7+5+3+1, 14+10+9+8+1, 14+10+9+8+2+1, 14+10+9+8+3+1, 14+10+9+8+5+1, 14+10+9+8+5+2+1, 14+10+9+8+5+3+1, 14+11+1, 14+11+2+1, 14+11+3+1, 14+11+5+1, 14+11+5+2+1, 14+11+5+3+1, 14+12+1, 14+12+2+1, 14+12+3+1, 14+12+5+1, 14+12+5+2+1, 14+12+5+3+1, 14+13+1, 14+13+2+1, 14+13+3+1, 14+13+5+1, 14+13+5+2+1, 14+13+5+3+1, 14+13+6+1, 14+13+6+2+1, 14+13+6+3+1, 14+13+6+5+1, 14+13+6+5+2+1, 14+13+6+5+3+1, 14+13+7+1, 14+13+7+2+1, 14+13+7+3+1, 14+13+7+5+1, 14+13+7+5+2+1, 14+13+7+5+3+1, 14+13+8+1, 14+13+8+2+1, 14+13+8+3+1, 14+13+8+5+1, 14+13+8+5+2+1, 14+13+8+5+3+1, 14+13+9+1, 14+13+9+2+1, 14+13+9+3+1, 14+13+9+5+1, 14+13+9+5+2+1, 14+13+9+5+3+1, 14+13+9+6+1, 14+13+9+6+2+1, 14+13+9+6+3+1, 14+13+9+6+5+1, 14+13+9+6+5+2+1, 14+13+9+6+5+3+1, 14+13+9+7+1, 14+13+9+7+2+1, 14+13+9+7+3+1, 14+13+9+7+5+1, 14+13+9+7+5+2+1, 14+13+9+7+5+3+1, 14+13+9+8+1, 14+13+9+8+2+1, 14+13+9+8+3+1, 14+13+9+8+5+1, 14+13+9+8+5+2+1, 14+13+9+8+5+3+1, 14+13+10+1, 14+13+10+2+1, 14+13+10+3+1, 14+13+10+5+1, 14+13+10+5+2+1, 14+13+10+5+3+1, 14+13+10+6+1, 14+13+10+6+2+1, 14+13+10+6+3+1, 14+13+10+6+5+1, 14+13+10+6+5+2+1, 14+13+10+6+5+3+1, 14+13+10+7+1, 14+13+10+7+2+1, 14+13+10+7+3+1, 14+13+10+7+5+1, 14+13+10+7+5+2+1, 14+13+10+7+5+3+1, 14+13+10+8+1, 14+13+10+8+2+1, 14+13+10+8+3+1, 14+13+10+8+5+1, 14+13+10+8+5+2+1, 14+13+10+8+5+3+1, 14+13+10+9+1, 14+13+10+9+2+1, 14+13+10+9+3+1, 14+13+10+9+5+1, 14+13+10+9+5+2+1, 14+13+10+9+5+3+1, 14+13+10+9+6+1, 14+13+10+9+6+2+1, 14+13+10+9+6+3+1, 14+13+10+9+6+5+1, 14+13+10+9+6+5+2+1, 14+13+10+9+6+5+3+1, 14+13+10+9+7+1, 14+13+10+9+7+2+1, 14+13+10+9+7+3+1, 14+13+10+9+7+5+1, 14+13+10+9+7+5+2+1, 14+13+10+9+7+5+3+1, 14+13+10+9+8+1, 14+13+10+9+8+2+1, 14+13+10+9+8+3+1, 14+13+10+9+8+5+1, 14+13+10+9+8+5+2+1, 14+13+10+9+8+5+3+1, 14+13+11+1, 14+13+11+2+1, 14+13+11+3+1, 14+13+11+5+1, 14+13+11+5+2+1, 14+13+11+5+3+1, 14+13+12+1, 14+13+12+2+1, 14+13+12+3+1, 14+13+12+5+1, 14+13+12+5+2+1, 14+13+12+5+3+1, 19+1, 19+2+1, 19+3+1, 19+5+1, 19+5+2+1, 19+5+3+1, 19+6+1, 19+6+2+1, 19+6+3+1, 19+6+5+1, 19+6+5+2+1, 19+6+5+3+1, 19+7+1, 19+7+2+1, 19+7+3+1, 19+7+5+1, 19+7+5+2+1, 19+7+5+3+1, 19+8+1, 19+8+2+1, 19+8+3+1, 19+8+5+1, 19+8+5+2+1, 19+8+5+3+1, 19+9+1, 19+9+2+1, 19+9+3+1, 19+9+5+1, 19+9+5+2+1, 19+9+5+3+1, 19+9+6+1, 19+9+6+2+1, 19+9+6+3+1, 19+9+6+5+1, 19+9+6+5+2+1, 19+9+6+5+3+1, 19+9+7+1, 19+9+7+2+1, 19+9+7+3+1, 19+9+7+5+1, 19+9+7+5+2+1, 19+9+7+5+3+1, 19+9+8+1, 19+9+8+2+1, 19+9+8+3+1, 19+9+8+5+1, 19+9+8+5+2+1, 19+9+8+5+3+1, 19+10+1, 19+10+2+1, 19+10+3+1, 19+10+5+1, 19+10+5+2+1, 19+10+5+3+1, 19+10+6+1, 19+10+6+2+1, 19+10+6+3+1, 19+10+6+5+1, 19+10+6+5+2+1, 19+10+6+5+3+1, 19+10+7+1, 19+10+7+2+1, 19+10+7+3+1, 19+10+7+5+1, 19+10+7+5+2+1, 19+10+7+5+3+1, 19+10+8+1, 19+10+8+2+1, 19+10+8+3+1, 19+10+8+5+1, 19+10+8+5+2+1, 19+10+8+5+3+1, 19+10+9+1, 19+10+9+2+1, 19+10+9+3+1, 19+10+9+5+1, 19+10+9+5+2+1, 19+10+9+5+3+1, 19+10+9+6+1, 19+10+9+6+2+1, 19+10+9+6+3+1, 19+10+9+6+5+1, 19+10+9+6+5+2+1, 19+10+9+6+5+3+1, 19+10+9+7+1, 19+10+9+7+2+1, 19+10+9+7+3+1, 19+10+9+7+5+1, 19+10+9+7+5+2+1, 19+10+9+7+5+3+1, 19+10+9+8+1, 19+10+9+8+2+1, 19+10+9+8+3+1, 19+10+9+8+5+1, 19+10+9+8+5+2+1, 19+10+9+8+5+3+1, 19+11+1, 19+11+2+1, 19+11+3+1, 19+11+5+1, 19+11+5+2+1, 19+11+5+3+1, 19+12+1, 19+12+2+1, 19+12+3+1, 19+12+5+1, 19+12+5+2+1, 19+12+5+3+1, 19+13+1, 19+13+2+1, 19+13+3+1, 19+13+5+1, 19+13+5+2+1, 19+13+5+3+1, 19+13+6+1, 19+13+6+2+1, 19+13+6+3+1, 19+13+6+5+1, 19+13+6+5+2+1, 19+13+6+5+3+1, 19+13+7+1, 19+13+7+2+1, 19+13+7+3+1, 19+13+7+5+1, 19+13+7+5+2+1, 19+13+7+5+3+1, 19+13+8+1, 19+13+8+2+1, 19+13+8+3+1, 19+13+8+5+1, 19+13+8+5+2+1, 19+13+8+5+3+1, 19+13+9+1, 19+13+9+2+1, 19+13+9+3+1, 19+13+9+5+1, 19+13+9+5+2+1, 19+13+9+5+3+1, 19+13+9+6+1, 19+13+9+6+2+1, 19+13+9+6+3+1, 19+13+9+6+5+1, 19+13+9+6+5+2+1, 19+13+9+6+5+3+1, 19+13+9+7+1, 19+13+9+7+2+1, 19+13+9+7+3+1, 19+13+9+7+5+1, 19+13+9+7+5+2+1, 19+13+9+7+5+3+1, 19+13+9+8+1, 19+13+9+8+2+1, 19+13+9+8+3+1, 19+13+9+8+5+1, 19+13+9+8+5+2+1, 19+13+9+8+5+3+1, 19+13+10+1, 19+13+10+2+1, 19+13+10+3+1, 19+13+10+5+1, 19+13+10+5+2+1, 19+13+10+5+3+1, 19+13+10+6+1, 19+13+10+6+2+1, 19+13+10+6+3+1, 19+13+10+6+5+1, 19+13+10+6+5+2+1, 19+13+10+6+5+3+1, 19+13+10+7+1, 19+13+10+7+2+1, 19+13+10+7+3+1, 19+13+10+7+5+1,

19+13+10+7+5+2+1, 19+13+10+7+5+3+1, 19+13+10+8+1, 19+13+10+8+2+1, 19+13+10+8+3+1, 19+13+10+8+5+1, 19+13+10+8+5+2+1, 19+13+10+8+5+3+1, 19+13+10+9+1, 19+13+10+9+2+1, 19+13+10+9+3+1, 19+13+10+9+5+1, 19+13+10+9+5+2+1, 19+13+10+9+5+3+1, 19+13+10+9+6+1, 19+13+10+9+6+2+1, 19+13+10+9+6+3+1, 19+13+10+9+6+5+1, 19+13+10+9+6+5+2+1, 19+13+10+9+6+5+3+1, 19+13+10+9+7+1, 19+13+10+9+7+2+1, 19+13+10+9+7+3+1, 19+13+10+9+7+5+1, 19+13+10+9+7+5+2+1, 19+13+10+9+7+5+3+1, 19+13+10+9+8+1, 19+13+10+9+8+2+1, 19+13+10+9+8+3+1, 19+13+10+9+8+5+1, 19+13+10+9+8+5+2+1, 19+13+10+9+8+5+3+1, 19+13+11+1, 19+13+11+2+1, 19+13+11+3+1, 19+13+11+5+1, 19+13+11+5+2+1, 19+13+11+5+3+1, 19+13+12+1, 19+13+12+2+1, 19+13+12+3+1, 19+13+12+5+1, 19+13+12+5+2+1, 19+13+12+5+3+1, 19+14+1, 19+14+2+1, 19+14+3+1, 19+14+5+1, 19+14+5+2+1, 19+14+5+3+1, 19+14+6+1, 19+14+6+2+1, 19+14+6+3+1, 19+14+6+5+1, 19+14+6+5+2+1, 19+14+6+5+3+1, 19+14+7+1, 19+14+7+2+1, 19+14+7+3+1, 19+14+7+5+1, 19+14+7+5+2+1, 19+14+7+5+3+1, 19+14+8+1, 19+14+8+2+1, 19+14+8+3+1, 19+14+8+5+1, 19+14+8+5+2+1, 19+14+8+5+3+1, 19+14+9+1, 19+14+9+2+1, 19+14+9+3+1, 19+14+9+5+1, 19+14+9+5+2+1, 19+14+9+5+3+1, 19+14+9+6+1, 19+14+9+6+2+1, 19+14+9+6+3+1, 19+14+9+6+5+1, 19+14+9+6+5+2+1, 19+14+9+6+5+3+1, 19+14+9+7+1, 19+14+9+7+2+1, 19+14+9+7+3+1, 19+14+9+7+5+1, 19+14+9+7+5+2+1, 19+14+9+7+5+3+1, 19+14+9+8+1, 19+14+9+8+2+1, 19+14+9+8+3+1, 19+14+9+8+5+1, 19+14+9+8+5+2+1, 19+14+9+8+5+3+1, 19+14+10+1, 19+14+10+2+1, 19+14+10+3+1, 19+14+10+5+1, 19+14+10+5+2+1, 19+14+10+5+3+1, 19+14+10+6+1, 19+14+10+6+2+1, 19+14+10+6+3+1, 19+14+10+6+5+1, 19+14+10+6+5+2+1, 19+14+10+6+5+3+1, 19+14+10+7+1, 19+14+10+7+2+1, 19+14+10+7+3+1, 19+14+10+7+5+1, 19+14+10+7+5+2+1, 19+14+10+7+5+3+1, 19+14+10+8+1, 19+14+10+8+2+1, 19+14+10+8+3+1, 19+14+10+8+5+1, 19+14+10+8+5+2+1, 19+14+10+8+5+3+1, 19+14+10+9+1, 19+14+10+9+2+1, 19+14+10+9+3+1, 19+14+10+9+5+1, 19+14+10+9+5+2+1, 19+14+10+9+5+3+1, 19+14+10+9+6+1, 19+14+10+9+6+2+1, 19+14+10+9+6+3+1, 19+14+10+9+6+5+1, 19+14+10+9+6+5+2+1, 19+14+10+9+6+5+3+1, 19+14+10+9+7+1, 19+14+10+9+7+2+1, 19+14+10+9+7+3+1, 19+14+10+9+7+5+1, 19+14+10+9+7+5+2+1, 19+14+10+9+7+5+3+1, 19+14+10+9+8+1, 19+14+10+9+8+2+1, 19+14+10+9+8+3+1, 19+14+10+9+8+5+1, 19+14+10+9+8+5+2+1, 19+14+10+9+8+5+3+1, 19+14+11+1, 19+14+11+2+1, 19+14+11+3+1, 19+14+11+5+1, 19+14+11+5+2+1, 19+14+11+5+3+1, 19+14+12+1, 19+14+12+2+1, 19+14+12+3+1, 19+14+12+5+1, 19+14+12+5+2+1, 19+14+12+5+3+1, 19+14+13+1, 19+14+13+2+1, 19+14+13+3+1, 19+14+13+5+1, 19+14+13+5+2+1, 19+14+13+5+3+1, 19+14+13+6+1, 19+14+13+6+2+1, 19+14+13+6+3+1, 19+14+13+6+5+1, 19+14+13+6+5+2+1, 19+14+13+6+5+3+1, 19+14+13+7+1, 19+14+13+7+2+1, 19+14+13+7+3+1, 19+14+13+7+5+1, 19+14+13+7+5+2+1, 19+14+13+7+5+3+1, 19+14+13+8+1, 19+14+13+8+2+1, 19+14+13+8+3+1, 19+14+13+8+5+1, 19+14+13+8+5+2+1, 19+14+13+8+5+3+1, 19+14+13+9+1, 19+14+13+9+2+1, 19+14+13+9+3+1, 19+14+13+9+5+1, 19+14+13+9+5+2+1, 19+14+13+9+5+3+1, 19+14+13+9+6+1, 19+14+13+9+6+2+1, 19+14+13+9+6+3+1, 19+14+13+9+6+5+1, 19+14+13+9+6+5+2+1, 19+14+13+9+6+5+3+1, 19+14+13+9+7+1, 19+14+13+9+7+2+1, 19+14+13+9+7+3+1, 19+14+13+9+7+5+1, 19+14+13+9+7+5+2+1, 19+14+13+9+7+5+3+1, 19+14+13+9+8+1, 19+14+13+9+8+2+1, 19+14+13+9+8+3+1, 19+14+13+9+8+5+1, 19+14+13+9+8+5+2+1, 19+14+13+9+8+5+3+1, 19+14+13+10+1, 19+14+13+10+2+1, 19+14+13+10+3+1, 19+14+13+10+5+1, 19+14+13+10+5+2+1, 19+14+13+10+5+3+1, 19+14+13+10+6+1, 19+14+13+10+6+2+1, 19+14+13+10+6+3+1, 19+14+13+10+6+5+1, 19+14+13+10+6+5+2+1, 19+14+13+10+6+5+3+1, 19+14+13+10+7+1, 19+14+13+10+7+2+1, 19+14+13+10+7+3+1, 19+14+13+10+7+5+1, 19+14+13+10+7+5+2+1, 19+14+13+10+7+5+3+1, 19+14+13+10+8+1, 19+14+13+10+8+2+1, 19+14+13+10+8+3+1, 19+14+13+10+8+5+1, 19+14+13+10+8+5+2+1, 19+14+13+10+8+5+3+1, 19+14+13+10+9+1, 19+14+13+10+9+2+1, 19+14+13+10+9+3+1, 19+14+13+10+9+5+1, 19+14+13+10+9+5+2+1, 19+14+13+10+9+5+3+1, 19+14+13+10+9+6+1, 19+14+13+10+9+6+2+1, 19+14+13+10+9+6+3+1, 19+14+13+10+9+6+5+1, 19+14+13+10+9+6+5+2+1, 19+14+13+10+9+6+5+3+1, 19+14+13+10+9+7+1, 19+14+13+10+9+7+2+1, 19+14+13+10+9+7+3+1, 19+14+13+10+9+7+5+1, 19+14+13+10+9+7+5+2+1, 19+14+13+10+9+7+5+3+1, 19+14+13+10+9+8+1, 19+14+13+10+9+8+2+1, 19+14+13+10+9+8+3+1, 19+14+13+10+9+8+5+1, 19+14+13+10+9+8+5+2+1, 19+14+13+10+9+8+5+3+1, 19+14+13+11+1, 19+14+13+11+2+1, 19+14+13+11+3+1, 19+14+13+11+5+1, 19+14+13+11+5+2+1, 19+14+13+11+5+3+1, 19+14+13+12+1, 19+14+13+12+2+1, 19+14+13+12+3+1, 19+14+13+12+5+1, 19+14+13+12+5+2+1, 19+14+13+12+5+3+1, 22+1, 22+2+1, 22+3+1, 22+5+1, 22+5+2+1, 22+5+3+1, 22+6+1, 22+6+2+1, 22+6+3+1, 22+6+5+1, 22+6+5+2+1, 22+6+5+3+1, 22+7+1, 22+7+2+1, 22+7+3+1, 22+7+5+1, 22+7+5+2+1, 22+7+5+3+1, 22+8+1, 22+8+2+1, 22+8+3+1, 22+8+5+1, 22+8+5+2+1, 22+8+5+3+1, 22+9+1, 22+9+2+1, 22+9+3+1, 22+9+5+1, 22+9+5+2+1, 22+9+5+3+1, 22+9+6+1, 22+9+6+2+1, 22+9+6+3+1, 22+9+6+5+1, 22+9+6+5+2+1, 22+9+6+5+3+1, 22+9+7+1, 22+9+7+2+1, 22+9+7+3+1, 22+9+7+5+1, 22+9+7+5+2+1, 22+9+7+5+3+1, 22+9+8+1, 22+9+8+2+1, 22+9+8+3+1, 22+9+8+5+1, 22+9+8+5+2+1, 22+9+8+5+3+1, 22+10+1, 22+10+2+1, 22+10+3+1, 22+10+5+1, 22+10+5+2+1, 22+10+5+3+1, 22+10+6+1, 22+10+6+2+1, 22+10+6+3+1, 22+10+6+5+1, 22+10+6+5+2+1, 22+10+6+5+3+1, 22+10+7+1, 22+10+7+2+1, 22+10+7+3+1, 22+10+7+5+1, 22+10+7+5+2+1, 22+10+7+5+3+1, 22+10+8+1, 22+10+8+2+1, 22+10+8+3+1, 22+10+8+5+1, 22+10+8+5+2+1, 22+10+8+5+3+1, 22+10+9+1, 22+10+9+2+1, 22+10+9+3+1, 22+10+9+5+1, 22+10+9+5+2+1, 22+10+9+5+3+1, 22+10+9+6+1, 22+10+9+6+2+1, 22+10+9+6+3+1, 22+10+9+6+5+1, 22+10+9+6+5+2+1, 22+10+9+6+5+3+1, 22+10+9+7+1, 22+10+9+7+2+1, 22+10+9+7+3+1, 22+10+9+7+5+1, 22+10+9+7+5+2+1, 22+10+9+7+5+3+1, 22+10+9+8+1, 22+10+9+8+2+1, 22+10+9+8+3+1, 22+10+9+8+5+1, 22+10+9+8+5+2+1, 22+10+9+8+5+3+1, 22+11+1, 22+11+2+1, 22+11+3+1, 22+11+5+1, 22+11+5+2+1, 22+11+5+3+1, 22+12+1, 22+12+2+1, 22+12+3+1, 22+12+5+1, 22+12+5+2+1, 22+12+5+3+1, 22+13+1, 22+13+2+1, 22+13+3+1, 22+13+5+1, 22+13+5+2+1, 22+13+5+3+1, 22+13+6+1, 22+13+6+2+1, 22+13+6+3+1, 22+13+6+5+1, 22+13+6+5+2+1, 22+13+6+5+3+1, 22+13+7+1, 22+13+7+2+1, 22+13+7+3+1, 22+13+7+5+1, 22+13+7+5+2+1, 22+13+7+5+3+1, 22+13+8+1, 22+13+8+2+1, 22+13+8+3+1, 22+13+8+5+1, 22+13+8+5+2+1, 22+13+8+5+3+1, 22+13+9+1, 22+13+9+2+1, 22+13+9+3+1, 22+13+9+5+1, 22+13+9+5+2+1, 22+13+9+5+3+1, 22+13+9+6+1, 22+13+9+6+2+1, 22+13+9+6+3+1, 22+13+9+6+5+1, 22+13+9+6+5+2+1, 22+13+9+6+5+3+1, 22+13+9+7+1, 22+13+9+7+2+1, 22+13+9+7+3+1, 22+13+9+7+5+1, 22+13+9+7+5+2+1, 22+13+9+7+5+3+1, 22+13+9+8+1, 22+13+9+8+2+1, 22+13+9+8+3+1, 22+13+9+8+5+1, 22+13+9+8+5+2+1, 22+13+9+8+5+3+1, 22+13+10+1, 22+13+10+2+1, 22+13+10+3+1, 22+13+10+5+1, 22+13+10+5+2+1, 22+13+10+5+3+1, 22+13+10+6+1, 22+13+10+6+2+1, 22+13+10+6+3+1, 22+13+10+6+5+1,

22+13+10+6+5+2+1, 22+13+10+6+5+3+1, 22+13+10+7+1, 22+13+10+7+2+1, 22+13+10+7+3+1, 22+13+10+7+5+1, 22+13+10+7+5+2+1, 22+13+10+7+5+3+1, 22+13+10+8+1, 22+13+10+8+2+1, 22+13+10+8+3+1, 22+13+10+8+5+1, 22+13+10+8+5+2+1, 22+13+10+8+5+3+1, 22+13+10+9+1, 22+13+10+9+2+1, 22+13+10+9+3+1, 22+13+10+9+5+1, 22+13+10+9+5+2+1, 22+13+10+9+5+3+1, 22+13+10+9+6+1, 22+13+10+9+6+2+1, 22+13+10+9+6+3+1, 22+13+10+9+6+5+1, 22+13+10+9+6+5+2+1, 22+13+10+9+6+5+3+1, 22+13+10+9+7+1, 22+13+10+9+7+2+1, 22+13+10+9+7+3+1, 22+13+10+9+7+5+1, 22+13+10+9+7+5+2+1, 22+13+10+9+7+5+3+1, 22+13+10+9+8+1, 22+13+10+9+8+2+1, 22+13+10+9+8+3+1, 22+13+10+9+8+5+1, 22+13+10+9+8+5+2+1, 22+13+10+9+8+5+3+1, 22+13+11+1, 22+13+11+2+1, 22+13+11+3+1, 22+13+11+5+1, 22+13+11+5+2+1, 22+13+11+5+3+1, 22+13+12+1, 22+13+12+2+1, 22+13+12+3+1, 22+13+12+5+1, 22+13+12+5+2+1, 22+13+12+5+3+1, 22+14+1, 22+14+2+1, 22+14+3+1, 22+14+5+1, 22+14+5+2+1, 22+14+5+3+1, 22+14+6+1, 22+14+6+2+1, 22+14+6+3+1, 22+14+6+5+1, 22+14+6+5+2+1, 22+14+6+5+3+1, 22+14+7+1, 22+14+7+2+1, 22+14+7+3+1, 22+14+7+5+1, 22+14+7+5+2+1, 22+14+7+5+3+1, 22+14+8+1, 22+14+8+2+1, 22+14+8+3+1, 22+14+8+5+1, 22+14+8+5+2+1, 22+14+8+5+3+1, 22+14+9+1, 22+14+9+2+1, 22+14+9+3+1, 22+14+9+5+1, 22+14+9+5+2+1, 22+14+9+5+3+1, 22+14+9+6+1, 22+14+9+6+2+1, 22+14+9+6+3+1, 22+14+9+6+5+1, 22+14+9+6+5+2+1, 22+14+9+6+5+3+1, 22+14+9+7+1, 22+14+9+7+2+1, 22+14+9+7+3+1, 22+14+9+7+5+1, 22+14+9+7+5+2+1, 22+14+9+7+5+3+1, 22+14+9+8+1, 22+14+9+8+2+1, 22+14+9+8+3+1, 22+14+9+8+5+1, 22+14+9+8+5+2+1, 22+14+9+8+5+3+1, 22+14+10+1, 22+14+10+2+1, 22+14+10+3+1, 22+14+10+5+1, 22+14+10+5+2+1, 22+14+10+5+3+1, 22+14+10+6+1, 22+14+10+6+2+1, 22+14+10+6+3+1, 22+14+10+6+5+1, 22+14+10+6+5+2+1, 22+14+10+6+5+3+1, 22+14+10+7+1, 22+14+10+7+2+1, 22+14+10+7+3+1, 22+14+10+7+5+1, 22+14+10+7+5+2+1, 22+14+10+7+5+3+1, 22+14+10+8+1, 22+14+10+8+2+1, 22+14+10+8+3+1, 22+14+10+8+5+1, 22+14+10+8+5+2+1, 22+14+10+8+5+3+1, 22+14+10+9+1, 22+14+10+9+2+1, 22+14+10+9+3+1, 22+14+10+9+5+1, 22+14+10+9+5+2+1, 22+14+10+9+5+3+1, 22+14+10+9+6+1, 22+14+10+9+6+2+1, 22+14+10+9+6+3+1, 22+14+10+9+6+5+1, 22+14+10+9+6+5+2+1, 22+14+10+9+6+5+3+1, 22+14+10+9+7+1, 22+14+10+9+7+2+1, 22+14+10+9+7+3+1, 22+14+10+9+7+5+1, 22+14+10+9+7+5+2+1, 22+14+10+9+7+5+3+1, 22+14+10+9+8+1, 22+14+10+9+8+2+1, 22+14+10+9+8+3+1, 22+14+10+9+8+5+1, 22+14+10+9+8+5+2+1, 22+14+10+9+8+5+3+1, 22+14+11+1, 22+14+11+2+1, 22+14+11+3+1, 22+14+11+5+1, 22+14+11+5+2+1, 22+14+11+5+3+1, 22+14+12+1, 22+14+12+2+1, 22+14+12+3+1, 22+14+12+5+1, 22+14+12+5+2+1, 22+14+12+5+3+1, 22+14+13+1, 22+14+13+2+1, 22+14+13+3+1, 22+14+13+5+1, 22+14+13+5+2+1, 22+14+13+5+3+1, 22+14+13+6+1, 22+14+13+6+2+1, 22+14+13+6+3+1, 22+14+13+6+5+1, 22+14+13+6+5+2+1, 22+14+13+6+5+3+1, 22+14+13+7+1, 22+14+13+7+2+1, 22+14+13+7+3+1, 22+14+13+7+5+1, 22+14+13+7+5+2+1, 22+14+13+7+5+3+1, 22+14+13+8+1, 22+14+13+8+2+1, 22+14+13+8+3+1, 22+14+13+8+5+1, 22+14+13+8+5+2+1, 22+14+13+8+5+3+1, 22+14+13+9+1, 22+14+13+9+2+1, 22+14+13+9+3+1, 22+14+13+9+5+1, 22+14+13+9+5+2+1, 22+14+13+9+5+3+1, 22+14+13+9+6+1, 22+14+13+9+6+2+1, 22+14+13+9+6+3+1, 22+14+13+9+6+5+1, 22+14+13+9+6+5+2+1, 22+14+13+9+6+5+3+1, 22+14+13+9+7+1, 22+14+13+9+7+2+1, 22+14+13+9+7+3+1, 22+14+13+9+7+5+1, 22+14+13+9+7+5+2+1, 22+14+13+9+7+5+3+1, 22+14+13+9+8+1, 22+14+13+9+8+2+1, 22+14+13+9+8+3+1, 22+14+13+9+8+5+1, 22+14+13+9+8+5+2+1, 22+14+13+9+8+5+3+1, 22+14+13+10+1, 22+14+13+10+2+1, 22+14+13+10+3+1, 22+14+13+10+5+1, 22+14+13+10+5+2+1, 22+14+13+10+5+3+1, 22+14+13+10+6+1, 22+14+13+10+6+2+1, 22+14+13+10+6+3+1, 22+14+13+10+6+5+1, 22+14+13+10+6+5+2+1, 22+14+13+10+6+5+3+1, 22+14+13+10+7+1, 22+14+13+10+7+2+1, 22+14+13+10+7+3+1, 22+14+13+10+7+5+1, 22+14+13+10+7+5+2+1, 22+14+13+10+7+5+3+1, 22+14+13+10+8+1, 22+14+13+10+8+2+1, 22+14+13+10+8+3+1, 22+14+13+10+8+5+1, 22+14+13+10+8+5+2+1, 22+14+13+10+8+5+3+1, 22+14+13+10+9+1, 22+14+13+10+9+2+1, 22+14+13+10+9+3+1, 22+14+13+10+9+5+1, 22+14+13+10+9+5+2+1, 22+14+13+10+9+5+3+1, 22+14+13+10+9+6+1, 22+14+13+10+9+6+2+1, 22+14+13+10+9+6+3+1, 22+14+13+10+9+6+5+1, 22+14+13+10+9+6+5+2+1, 22+14+13+10+9+6+5+3+1, 22+14+13+10+9+7+1, 22+14+13+10+9+7+2+1, 22+14+13+10+9+7+3+1, 22+14+13+10+9+7+5+1, 22+14+13+10+9+7+5+2+1, 22+14+13+10+9+7+5+3+1, 22+14+13+10+9+8+1, 22+14+13+10+9+8+2+1, 22+14+13+10+9+8+3+1, 22+14+13+10+9+8+5+1, 22+14+13+10+9+8+5+2+1, 22+14+13+10+9+8+5+3+1, 22+14+13+11+1, 22+14+13+11+2+1, 22+14+13+11+3+1, 22+14+13+11+5+1, 22+14+13+11+5+2+1, 22+14+13+11+5+3+1, 22+14+13+12+1, 22+14+13+12+2+1, 22+14+13+12+3+1, 22+14+13+12+5+1, 22+14+13+12+5+2+1, 22+14+13+12+5+3+1.

In the list above the numbers refer to the embodiments according to their numbering provided hereinabove whereas "+" indicates the dependency from another embodiment. The different individualized embodiments are separated by commas. In other words, "5+2+1" for example refers to embodiment 5) depending on embodiment 2), depending on embodiment 1), i.e. embodiment "5+2+1" corresponds to embodiment 5) further characterized by the features of the embodiments 2) and 1).

Abbreviations (as Used Hereinbefore or Hereinafter):

aq. aqueous atm Atmosphere

Bu Butyl such as in tBu=tert-butyl=tertiary butyl

ELSD Evaporative Light-Scattering Detection eq Equivalent(s)

ES Electron spray

FC Flash Chromatography on silica gel

Fig Figure h Hour(s)

$^1$H-NMR Nuclear magnetic resonance of the proton

HPLC High performance liquid chromatography

LC-MS Liquid chromatography-Mass Spectroscopy

M Exact mass (as used for LC-MS)

MeCN Acetonitrile

MeOH Methanol

MHz Megahertz

µl microliter min Minute(s)

MS Mass spectroscopy

N Normality prep. Preparative

PSD Particle size distribution

RH relative humidity

RT Room temperature sat. Saturated $t_R$ Retention time

UV Ultra violet

Experimental Part

All temperatures are stated in ° C.

LC-MS

For example, the following conditions may be used: Apparatus: Agilent 1100 series with mass spectroscopy detection (MS: Finnigan single quadrupole). Column: Agilent Zorbax SB-Aq, (3.5 um, 4.6×50 mm). Conditions: MeCN [eluent A]; water+0.04% TFA [eluent B].

Gradient: 95% B→5% B over 1.5 min. (flow: 4.5 ml/min.). Detection: UV+MS.

X-ray powder diffraction analysis (XRPD)

X-ray powder diffraction patterns were collected on a Bruker D8 Advance X-ray diffractometer equipped with a Lynxeye detector operated with $CuK_\alpha$-radiation in reflection mode (coupled two Theta/Theta). Typically, the X-ray tube was run at of 40 kV/40 mA. A step size of 0.02° (2θ) and a step time of 76.8 sec over a scanning range of 3-50° in 2θ were applied. The divergence slit was set to fixed 0.3. Powders were slightly pressed into a silicon single crystal sample holder with depth of 0.5 mm and samples were rotated in their own plane during the measurement. Diffraction data are reported using combined Cu Kα1 and Kα2 radiation, without Kα2 stripping. The accuracy of the 2θ values as provided herein is in the range of +/−0.1-0.2° as it is generally the case for conventionally recorded X-ray powder diffraction patterns.

Gravimetric vapour sorption (GVS) analysis

Measurements were performed on a multi sample instrument SPS-100n (Projekt Messtechnik, Ulm, Germany) operated in stepping mode at 25° C. The sample was allowed to equilibrate at 40% RH before starting a pre-defined humidity program (40-0-95-0-95-40% RH, steps of 5% ΔRH and with a maximal equilibration time of 24 hours per step were applied. About 20 to 30 mg of each sample was used. The hygroscopic classification is done according to the European Pharmacopeia 8.0, e.g., slightly hygroscopic: increase in mass is less than 2% and equal to or greater than 0.2% mass/mass; hygroscopic: increase in mass is less than 15% and equal to or greater than 2% mass/mass. The mass change between 40% relative humidity and 80% relative humidity in the first adsorption scan is considered.

Differential scanning calorimetry (DSC)

DSC data were collected on a Mettler Toledo STARe System (DSC822e module, measuring cell with ceramic sensor and STAR software version 9.20) equipped with a 34-position auto-sampler. The instrument was calibrated for energy and temperature using certified indium. Typically 1-5 mg of each sample, in an automatically pierced aluminium pan, was heated at 10° C. $min^{-1}$, unless stated otherwise, from −20° C. to 280° C. A nitrogen purge at 20 ml $min^{-1}$ was maintained over the sample. Peak temperatures are reported for melting points.

Thermogravimetric analysis (TGA)

TGA data were collected on a Mettler Toledo STARe System (TGA851e module and STAR software version 9.20) equipped with a 34-position auto-sampler. Typically, about 5 mg of a sample, in an automatically pierced aluminium pan, was heated at 10° C. $min^{-1}$, unless stated otherwise, from 30° C. to 250° C. A nitrogen purge at 10 ml $min^{-1}$ was maintained over the sample.

Particle size distribution (PSD)

PSD measurements were performed by laser-difraction using a wet dispersion method. Data were collected on a Mastersizer 2000 (Malvern) equipped with a dispersion unit Hydro 2000S in the size range from 0.020 μm to 2000.000 μm. Typically, about 100 mg sample in about 20 ml Tegiloxan 3 (silicon oil, CAS Nr. 9016-00-6) is dispersed in an ultrasonic bad for about 30 s and subsequently added to a prefilled with Tegiloxan 3 dispersion unit until obscuration of about 10% to about 30% is achieved. After a circulation time of 5 min, a sample measurement is performed. Reported particle size values (D10, D50 and D90) represent an average value of 3 measurements.

Reference Example 1

COMPOUND can be prepared as a white to off-white powder using the process disclosed in WO2004/054975.

The process disclosed in WO2004/054975 may optionally comprise isolation of the compound of formula (III) as described in WO2004/054975 in the form of benzenesulfonic acid salt. For example, (2R,3S,4R,5S)-3,4,5-tris(benzyloxy)-2-((benzyloxy)methyl)-1-butylpiperidin-1-ium benzenesulfonate of the following formula

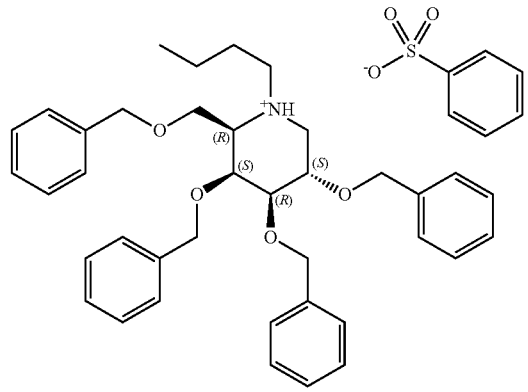

can be prepared as follows:
(2R,3S,4R,5S)-3,4,5-Tris(benzyloxy)-2-((benzyloxy)methyl)-1-butylpiperidine (20.0 g) was dissolved in TBME (100 mL) and MeOH (6 mL), then cooled to 0° C. A solution of benzenesulfonic acid (4.37 g) in TBME (40 mL) was prepared. Half of this solution (20 mL) was added at 0° C. over 30 min. After holding at 0° C. for 30 min, the remaining solution of benzenesulfonic acid (20 mL) was added over 30 min. The suspension was stirred at 0° C. for another 30 min, filtered and rinsed with cold TBME (40 mL). The filter cake was dried to afford (2R,3S,4R,5S)-3,4,5-tris(benzyloxy)-2-((benzyloxy)methyl)-1-butylpiperidin-1-ium benzenesulfonate (13.15 g, 52% yield) as off-white crystals (1H NMR (500 MHz, DMSO-d6): 7.63-7.61 (m, 2H), 7.43-7.28 (m, 23H), 4.87-4.58 (m, 6H), 4.54-4.44 (m, 3H), 4.02-3.97 (m, 1H), 3.95-3.87 (m, 1H), 3.81-3.73 (m, 3H), 3.15-3.00 (m, 2H), 1.70-1.53 (m, 2H), 1.26-1.12 (m, 2H), 0.85-0.81 (m, 3H); MS (ESI): m/z=580.4 [M+H]+; m.p. 91.5° C. as determined by DSC; and X-ray powder diffraction diagram having peaks at the following angles of refraction 2θ: 6.01° (100%), 11.1° (11%), 12.0° (11%), 12.6° (5%), 13.4° (6%), 13.9° (9%), 16.3° (8%), 16.9° (12%), 17.8° (9%), and 20.7° (66%).

Example 1: Preparation of COMPOUND in Crystalline Form 1

Solvent quantities for the crystallization are calculated based on the content of the measured (e.g. by LC-MS) content of COMPOUND (weight in kg=M), in crude solution of Reference Example 1, as follows:

amount of methanol (kg): S1=M×0.72
amount of water (kg): S2=M×0.24
amount of acetone, first portion (kg): S3=M×3.6
amount of acetone, second portion (kg): S4=M×5.4
amount of acetone, washing (kg): S5=M×2

To the oily residue of crude COMPOUND as disclosed in WO2004/054975 (p.9, l.22), add at room temperature the appropriate amount of methanol (=S1), the appropriate amount of water (=S2), the appropriate amount of dry acetone (=S3), in order to get a suspension. Heat the suspension to reflux (55° C.-57° C.) in order to dissolve the crude product. While maintaining the temperature at 55° C., slowly dose (over 2 hours) the appropriate amount of acetone (=S4). Cool the suspension to 40° C. within 60 min., stir at 40° C. for 15 min. If no crystals are formed, add seed crystals, then start cooling to 0° C. within 2 h and keep stirring for 2 h at 0° C. Collect the product by filtration and wash the filter cake with 3×the appropriate amount of acetone (=S5) at 5° C. Dry under vacuum at 40° C. for 20 h.

Example 2: Preparation of COMPOUND in Crystalline Form 1

Solvent quantities for the crystallization are calculated based on the content of the measured (e.g. by LC-MS) content of COMPOUND (weight in kg=M), in crude solution of Reference Example 1, as follows:
amount of isopropanol (kg): S1=M×1.18
amount of anhydrous acetone (kg): S2=M×4.95
amount of anhydrous acetone (kg): S3=M×2.67
amount of methanol (kg): S4=M×2.24
amount of methanol (kg): S5=M×0.88
amount of water (kg): S6=M×0.06
amount of ethyl acetate (kg) S7=M×2.13
amount of ethyl acetate (kg) S8=M×0.23
activated charcoal (kg)=M×0.13

Step 1: The oily residue of crude COMPOUND as disclosed in WO2004/054975 (p.9, l.22) is dissolved in isopropanol (=S1) and heated to 55° C. While keeping the temperature in the range 50° C.-56° C., anhydrous acetone (=S2) is added during 30 min. The resulting solution is cooled to 0° C. at a constant rate of 0.27° C./min and the obtained suspension is stirred for 2 hours. The product is collected by filtration. The filter cake is washed with anhydrous acetone (=S3) at 0° C. and then dried under reduced pressure of less than 40 mbar at 30° C. for 18 h.

Step 2: The product of step 1 is dissolved in methanol (=S4) at 45° C. and filtered over activate charcoal (Norit™ SX1). The resulting solution is concentrated by vacuum destilation at temperature below or equal to 45° C. until no destilate is observed. The destillation residue is dissolved in methanol (=S5) and water (=S6), and the resulting solution is warmed up to 56° C. While keeping the temperature, ethyl acetate (=S7) is added during 30 min. The resulting suspension is cooled to 0° C. at a constant rate of 0.9° C./min and stirred for 2 hours at 0° C. White crystalline material of COMPOUND is collected by filtration, washed twice with ethyl acetate (=S8) at 0° C. and dried under reduced pressure of less than 40 mbar at 30° C.

Reference Example 3: Preparation of COMPOUND in Crystalline Form 1

Solvent quantities for the crystallization are calculated based on the content of the measured (e.g. by LC-MS) content of COMPOUND (weight in kg=M), in crude solution of Reference Example 1, as follows:
amount of anhydrous acetone (kg): S1=M×3.14
water (kg): S2=M×0.05
amount of anhydrous acetone (kg): S3=M×3.14
amount of anhydrous acetone (kg): S4=M×3.14
methanol (kg): S5=M×0.54
water (kg): S6=M×0.13
activated carbon (kg): S7=M×0.05
anhydrous acetone (kg): S8=M×1.28
anhydrous acetone (kg): S9=M×0.85
anhydrous acetone (kg): S10=M×2.96
anhydrous acetone (kg): S11=M×0.85

Step 1: To the oily residue of crude COMPOUND as disclosed in WO2004/054975 (p.9, l.22), add at room temperature the appropriate amount of anhydrous acetone (=S1) in order to get a suspension. Heat the suspension to reflux (57° C.) in order to dissolve the crude product and carefully add water (=S2) until a clear solution is obtained. Add further anhydrous acetone (=S3) and cool to 40° C. within 60 min. and further stir at 40° C. for 15 min. If no crystals are formed, add seed crystals, then start cooling to 0° C. within 2 h under stirring for additional 2 h. at 0° C. Collect the product by filtration and wash the filter cake with anhydrous acetone (=S4).

Step 2: Dissolve the product of step 1 in methanol (=S5) and water (=S6), heat to 60° C. to obtain a solution. Optionally treat this solution with activated carbon (=S7) for 30 minutes and filter. To the warm solution add anhydrous acetone (=S8) during 30 min. Keep refluxing for 30 min. (ca. 57° C.). To this mixture add acetone (=S9), followed by seed crystals (only in case no crystal formation is observed). Then stir and dose over 2 h anhydrous acetone (=S10). Cool the suspension to −5° C. within 4 h, then agitate for 2 h at −5° C. Collect the product by filtration and wash the filter cake twice with anhydrous acetone (=S11) at −5° C. Dry under vacuum to constant weight.

TABLE 2

Characterisation data for COMPOUND in crystalline form 1

| Technique | Data Summary | Remarks |
| --- | --- | --- |
| XRPD | Crystalline | see FIG. 1 |
| 1H-NMR | Consistent | — |
| DSC | Endothermal melting with peak at 130° C. | — |
| TGA | Mass loss of <0.1% in the range 31.5 to 140° C. | — |
| Hygroscopicity | Not hygroscopic | — |

Particle size data for COMPOUND in crystalline form 1

Particle size measurements of COMPOUND in crystalline form 1 as obtained in Examples 1, 2 and Reference Example 3 are performed using the method described herein. Each data point in Table 3 represents an average value obtained from at least five separate crystallization batches, each measured in triplicate.

TABLE 3

|  | D10 [µm] | D50 [µm] | D90 [µm] |
| --- | --- | --- | --- |
| Example 1 | 11 | 79 | 169 |
| Example 2 | 7 | 57 | 138 |
| Reference Example 3 | 7 | 22 | 42 |

Example 4: Preparation of Capsules Comprising COMPOUND in Crystalline Form 1

COMPOUND according to the present invention and lactose anhydrous are mixed, sieved on an impeller mill (e.g. 1 mm smooth screen) and blended using a diffusion blender (e.g. 100 revolutions). In a separate step talc is sieved (e.g. 1 mm smooth screen) and added to the blend. The resulting mixture is blended once again (e.g. 100 revolutions). The final blend is transferred to an encapsulator, in particular a donator type machine and filled into hard gelatin capsules. Table 4 summarizes typical production process amounts.

TABLE 4

| Material | Additional information | Amount (80 kg batch) | Unit dose |
|---|---|---|---|
| COMPOUND according to the present invention | Active ingredient | 45.45 kg | 250 mg |
| Lactose anhydrous | Diluent | 30.55 kg | 168 mg |
| Talc | Lubricant | 4.00 kg | 22 mg |
| Hard gelatine capsules | Size 0 | 180 000 capsules | 1 capsule |

Pharmaceutical preparations comprising crystalline COMPOUND according to the present invention, such as powder blends (in particular, capsules comprising such powder blends) may be prepared in various ways. However, certain physical/chemical properties of COMPOUND according to the present invention and/or certain physical/chemical properties of the final blend and/or certain physical/chemical properties of the capsule may lead to advantageous properties such as those defined hereinabove. For example, the density (tapped and/or bulk) of pharmaceutical compositions according to the present invention may be especially advantageous, in particular for preparing capsules.

Purity of COMPOUND in crystalline form 1

Purity determination of COMPOUND in crystalline form 1 as obtained in Examples 1 and 2 is performed using the HPLC method described herein. Each data point in Table 5 represents an average value obtained from at least five separate crystallization batches.

TABLE 5

| | Total impurity [%] | Main impurity - (2R,3S,4R,5R)-1-butyl-2-(hydroxymethyl)-piperidine-3,4,5-triol [%] |
|---|---|---|
| Example 1 | 0.52 | 0.43 |
| Example 2 | 0.33 | 0.18 |

The invention claimed is:
1. A crystalline form of the compound f(2R,3S,4R,5S)-1-butyl-2-(hydroxymethyl)piperidine-3,4,5-triol:

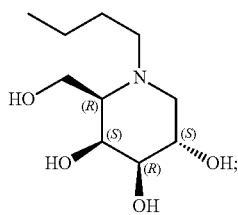

characterized by the presence of peaks in the X-ray powder diffraction diagram at the following angles of refraction 2θ: 5.6°, 17.7°, and 21.5°; wherein said X-ray powder diffraction diagram is obtained by using combined Cu Kα1 and Kα2 radiation, without Kα2 stripping; and the accuracy of the 2θ values is in the range of 2θ+/−0.2°.

2. A crystalline form of the compound according to claim 1, characterized by the presence of peaks in the X-ray powder diffraction diagram at the following angles of refraction 2θ: 5.6° 12.4°, 14.8°, 17.7°, and 21.5°; wherein said X-ray powder diffraction diagram is obtained by using combined Cu Kα1 and Kα2 radiation, without Kα2 stripping; and the accuracy of the 2θ values is in the range of 2θ+/−0.2°.

3. A crystalline form of the compound according to claim 1, characterized by the presence of peaks in the X-ray powder diffraction diagram at the following angles of refraction 2θ: 5.6° 12.4°, 13.4°, 14.8°, 16.8°, 17.7°, 19.4°, 21.5°, 22.1°, and 24.2°; wherein said X-ray powder diffraction diagram is obtained by using combined Cu Kα1 and Kα2 radiation, without Kα2 stripping; and the accuracy of the 2θ values is in the range of 2θ+/−0.2°.

4. A crystalline form of the compound according to claim 1, which essentially shows the X-ray powder diffraction pattern as depicted in FIG. 1.

5. A crystalline form of the compound according to claim 1, wherein said crystalline form shows endothermal melting with a peak at about 130° C. as determined by differential scanning calorimetry.

6. A crystalline form of the compound according to claim 1, wherein said crystalline form consists essentially of particles having a particle size distribution, wherein D50 is equal or greater than about 50 μm.

7. A crystalline form of the compound according to claim 1, wherein said crystalline form consists essentially of particles having a particle size distribution, wherein
   D50 is from about 50 μm to about 150 μm; and
   D90 is from about 100 μm to about 400 μm.

8. A process for the preparation of the crystalline form of the compound according to claim 1, wherein said process comprises:
   I) Step 1 comprising:
      i. Preparing a solution of (2R,3S,4R,5S)-1-butyl-2-(hydroxymethyl)piperidine-3,4,5-triol in isopropanol, wherein preferably about 100 ww % to 140 ww % of isopropanol with respect to the weight of (2R,3S,4R,5S)-1-butyl-2-(hydroxymethyl)piperidine-3,4,5-triol is used;
      ii. Warming up the solution to about 45° C. to 60° C.;
      iii. Adding anhydrous acetone, wherein about 450 ww % to 550 ww % with respect to the weight of (2R,3S,4R,5S)-1-butyl-2-(hydroxymethyl)piperidine-3,4,5-triol is added, and wherein said acetone is added during about 30 min;
      iv. Cooling the obtained solution to about −5° C. to +5° C. at a constant rate;
      v. Agitating at about 0° C. for 1 to 3 hours;
      vi. Isolating the product by solid-liquid separation;
      vii. Washing the solid with anhydrous acetone, wherein about 250 ww % to 300 ww % of acetone with respect to the weight of (2R,3S,4R,5S)-1-butyl-2-(hydroxymethyl)piperidine-3,4,5-triol is used; and
      viii. Drying; and
   II) Step 2 comprising:
      i. Dissolving the product of the first crystallization step at about 45° C. in about 200 ww % to 250 ww % methanol with respect to the weight of (2R,3S,4R,5S)-1-butyl-2-(hydroxymethyl)piperidine-3,4,5-triol;
ii. Filtering over activated carbon;
iii. Washing the activated carbon with about 90 ww % of methanol with respect to the weight of (2R,3S,4R,5S)-1-butyl-2-(hydroxymethyl)piperidine-3,4,5-triol;
iv. Concentrating the solution under vacuum;
v. Dissolving the distillation residue of the previous step in about 60 ww % to 65 ww % methanol and about 4 ww % to 8 ww % water with respect to the weight of (2R,3S,4R,5S)-1-butyl-2-(hydroxymethyl)piperidine-3,4,5-triol;
vi. Warming up the solution to about 55° C. to 58° C.
vii. Adding about 200 ww % to 220 ww % ethyl acetate during about 25 min to 45 min while keeping the temperature between about 55° C. to 58° C.;
viii. Cooling the resulting suspension down to about −5 to +5° C. at a constant rate;
ix. Agitating at about 0° C. for 1.5 to 3 hours;
x. Isolating the product by solid-liquid separation;
xi. Washing the solid twice with ethyl acetate; and
xii. Drying.

9. A pharmaceutical composition comprising:
from about 55 ww % to about 75 ww % of the crystalline form of the compound according to claim 1; and
from about 24 ww % to about 44 ww % of one or more diluents selected from a group consisting of lactose anhydrous, silicified microcrystalline cellulose, microcrystalline cellulose, calcium hydrogen phosphate and isomalt;
from 0 ww % to about 6 ww % of a component selected from a group consisting of talc, magnesium stearate, sodium stearyl fumarate, silicon dioxide, or a combination thereof;
where the total ww % of said pharmaceutical composition is 100.

10. A pharmaceutical composition according to claim 9, comprising:
from about 55 ww % to about 75 ww % of the crystalline form of the compound according to claim 1;
from about 24 ww % to about 44 ww % of lactose anhydrous; and
from 0 ww % to about 6 ww % of a component selected from a group consisting of talc, magnesium stearate, sodium stearyl fumarate, silicon dioxide, or a combination thereof,
where the total ww % of said pharmaceutical composition is 100.

11. A capsule comprising the pharmaceutical composition according to claim 9.

12. A method of reducing or eliminating symptoms of Niemann-Pick type C disease; Gaucher disease types 1, 2 and 3; Tay-Sachs disease, Sandhoff disease, GM2 gangliosidosis AB variant; GM1 gangliosidosis; Fabry disease; Schindler disease; Smith-Lemly-Opitz syndrome; Tangier disease; mucolipidosis IV; mucopolysaccharidoses; GbA1-synucleopathies and syndromes thereof; Huntington's disease; polycystic kidney disease; Darier's disease; or Guillain-Barré syndrome the method comprising administering to a patient in need thereof a pharmaceutically effective amount of the crystalline form of the compound according to claim 1.

13. A method of reducing or eliminating symptoms of Fabry disease, comprising administering to a patient in need thereof an effective amount of a crystalline form of the compound according to claim 1.

14. A crystalline form of the compound according to claim 1, wherein said crystalline form consists essentially of particles having a particle size distribution, wherein D50 is from about 50 μm to about 300 μm.

15. A crystalline form of the compound according to claim 1, wherein said crystalline form has a total impurity amount of less than about 0.5%.

16. A crystalline form of the compound according to claim 2, wherein said crystalline form shows endothermal melting with a peak at about 130° C. as determined by differential scanning calorimetry.

17. A crystalline form of the compound according to claim 2, wherein said crystalline form consists essentially of particles having a particle size distribution, wherein D50 is equal or greater than about 50 μm.

18. A crystalline form of the compound according to claim 2, wherein said crystalline form consists essentially of particles having a particle size distribution wherein D50 is equal or greater than about 70 μm.

19. A crystalline form of the compound according to claim 2, wherein said crystalline form consists essentially of particles having a particle size distribution, wherein D50 is from about 50 μm to about 300 μm.

20. A crystalline form of the compound according to claim 2, wherein said crystalline form consists essentially of particles having a particle size distribution, wherein D50 is from about 70 μm to about 250 μm.

21. A crystalline form of the compound according to claim 2, wherein said crystalline form consists essentially of particles having a particle size distribution, wherein
D50 is from about 50 μm to about 300 μm; and
D90 is from about 100 μm to about 400 μm.

22. A crystalline form of the compound according to claim 2, wherein said crystalline form consists essentially of particles having a particle size distribution, wherein
D50 is from about 50 μm to about 300 μm; and
D90 is from about 100 μm to about 400 μm;
and D10 is from about 3 μm to about 12 μm.

23. A crystalline form of the compound according to claim 3, wherein said crystalline form consists essentially of particles having a particle size distribution, wherein D50 is equal or greater than about 50 μm.

24. A crystalline form of the compound according to claim 3, wherein said crystalline form consists essentially of particles having a particle size distribution, wherein D50 is from about 50 μm to about 300 μm.

25. A crystalline form of the compound according to claim 3, wherein said crystalline form consists essentially of particles having a particle size distribution, wherein D50 is from about 70 μm to about 250 μm.

26. A crystalline form of the compound according to claim 3, wherein said crystalline form consists essentially of particles having a particle size distribution, wherein
D50 is from about 50 μm to about 300 μm; and
D90 is from about 100 μm to about 400 μm.

27. A pharmaceutical composition according to claim 10, wherein the tapped density of said pharmaceutical composition is at least 0.64 g/mL.

28. A pharmaceutical composition comprising:
from about 55 ww % to about 75 ww % of the crystalline form of the compound according to claim 2; and
from about 24 ww % to about 44 ww % of one or more diluents selected from a group consisting of lactose anhydrous, silicified microcrystalline cellulose, microcrystalline cellulose, calcium hydrogen phosphate and isomalt; and
from 0 ww % to about 6 ww % of a component selected from a group consisting of talc, magnesium stearate, sodium stearyl fumarate, silicon dioxide, or a combination thereof;
where the total ww % of said pharmaceutical composition is 100.

29. A pharmaceutical composition according to claim 28, wherein the tapped density of said pharmaceutical composition is at least 0.64 g/mL.

30. A pharmaceutical composition comprising:
from about 55 ww % to about 75 ww % of the crystalline form of the compound according to claim 2;
from about 24 ww % to about 44 ww % of lactose anhydrous; and
from 0 ww % to about 6 ww % of a component selected from a group consisting of talc, magnesium stearate, sodium stearyl fumarate, silicon dioxide, or a combination thereof where the total ww % of said pharmaceutical composition is 100.

31. A pharmaceutical composition according to claim 30, wherein the tapped density of said pharmaceutical composition is at least 0.64 g/mL.

32. A pharmaceutical composition comprising:
from about 55 ww % to about 75 ww % of the crystalline form of the compound according to claim 17; and
from about 24 ww % to about 44 ww % of one or more diluents selected from a group consisting of lactose anhydrous, silicified microcrystalline cellulose, microcrystalline cellulose, calcium hydrogen phosphate and isomalt; and
from 0 ww % to about 6 ww % of a component selected from a group consisting of talc, magnesium stearate, sodium stearyl fumarate, silicon dioxide, or a combination thereof;
where the total ww % of said pharmaceutical composition is 100.

33. A pharmaceutical composition according to claim 32, wherein the tapped density of said pharmaceutical composition is at least 0.64 g/mL.

34. A pharmaceutical composition comprising:
from about 55 ww % to about 75 ww % of the crystalline form of the compound according to claim 17;
from about 24 ww % to about 44 ww % of lactose anhydrous; and
from 0 ww % to about 6 ww % of a component selected from a group consisting of talc, magnesium stearate, sodium stearyl fumarate, silicon dioxide, or a combination thereof where the total ww % of said pharmaceutical composition is 100.

35. A pharmaceutical composition according to claim 34, wherein the tapped density of said pharmaceutical composition is at least 0.64 g/mL.

36. A pharmaceutical composition comprising:
from about 55 ww % to about 75 ww % of the crystalline form of the compound according to claim 19;
from about 24 ww % to about 44 ww % of lactose anhydrous; and
from 0 ww % to about 6 ww % of a component selected from a group consisting of talc, magnesium stearate, sodium stearyl fumarate, silicon dioxide, or a combination thereof where the total ww % of said pharmaceutical composition is 100.

37. A pharmaceutical composition comprising:
from about 55 ww % to about 75 ww % of the crystalline form of the compound according to claim 21;
from about 24 ww % to about 44 ww % of lactose anhydrous; and
from 0 ww % to about 6 ww % of a component selected from a group consisting of talc, magnesium stearate, sodium stearyl fumarate, silicon dioxide, or a combination thereof where the total ww % of said pharmaceutical composition is 100.

38. A pharmaceutical composition according to claim 37, wherein the tapped density of said pharmaceutical composition is at least 0.64 g/mL.

39. A pharmaceutical composition comprising:
from about 55 ww % to about 75 ww % of the crystalline form of the compound according to claim 23;
from about 24 ww % to about 44 ww % of lactose anhydrous; and
from 0 ww % to about 6 ww % of a component selected from a group consisting of talc, magnesium stearate, sodium stearyl fumarate, silicon dioxide, or a combination thereof where the total ww % of said pharmaceutical composition is 100.

40. A pharmaceutical composition comprising:
from about 55 ww % to about 75 ww % of the crystalline form of the compound according to claim 24;
from about 24 ww % to about 44 ww % of lactose anhydrous; and
from 0 ww % to about 6 ww % of a component selected from a group consisting of talc, magnesium stearate, sodium stearyl fumarate, silicon dioxide, or a combination thereof where the total ww % of said pharmaceutical composition is 100.

41. A capsule comprising the pharmaceutical composition according to claim 28.

42. A capsule comprising the pharmaceutical composition according to claim 29.

43. A capsule comprising the pharmaceutical composition according to claim 30.

44. A capsule comprising the pharmaceutical composition according to claim 31.

45. A capsule according to claim 44, wherein said capsule comprises said compound in an amount of about 250 mg of active ingredient per capsule.

46. A capsule according to claim 45, wherein said capsule is a size 0 capsule.

47. A capsule comprising the pharmaceutical composition according to claim 32.

48. A capsule comprising the pharmaceutical composition according to claim 33.

49. A capsule according to claim 48, wherein said capsule comprises said compound in an amount of about 250 mg of active ingredient per capsule.

50. A capsule according to claim 49, wherein said capsule is a size 0 capsule.

51. A capsule comprising the pharmaceutical composition according to claim 34.

52. A capsule according to claim 51, wherein said capsule comprises said compound in an amount of about 250 mg of active ingredient per capsule.

53. A capsule according to claim 52, wherein said capsule is a size 0 capsule.

54. A capsule comprising the pharmaceutical composition according to claim 35.

55. A capsule according to claim 54, wherein said capsule comprises said compound in an amount of about 250 mg of active ingredient per capsule.

56. A capsule according to claim 55, wherein said capsule is a size 0 capsule.

57. A method of reducing or eliminating symptoms of Fabry disease, comprising administering to a patient in need thereof an effective amount of a crystalline form of the compound (2R,3S,4R,5S)-1-butyl-2-(hydroxymethyl)piperidine-3,4,5-triol, wherein said compound is administered in the form of a capsule according to claim 42.

58. A method of reducing or eliminating symptoms of Fabry disease, comprising administering to a patient in need thereof an effective amount of a crystalline form of the compound (2R,3S,4R,5S)-1-butyl-2-(hydroxymethyl)piperidine-3,4,5-triol, wherein said compound is administered in the form of a capsule according to claim 43.

59. A method of reducing or eliminating symptoms of Fabry disease, comprising administering to a patient in need thereof an effective amount of a crystalline form of the compound (2R,3S,4R,5S)-1-butyl-2-(hydroxymethyl)piperidine-3,4,5-triol, wherein said compound is administered in the form of a capsule according to claim 44.

60. A method of reducing or eliminating symptoms of Fabry disease, comprising administering to a patient in need thereof an effective amount of a crystalline form of the compound (2R,3S,4R,5S)-1-butyl-2-(hydroxymethyl)piperidine-3,4,5-triol, wherein said compound is administered in the form of a capsule according to claim 48.

61. A method of reducing or eliminating symptoms of Fabry disease, comprising administering to a patient in need thereof an effective amount of a crystalline form of the compound (2R,3S,4R,5S)-1-butyl-2-(hydroxymethyl)piperidine-3,4,5-triol, wherein said compound is administered in the form of a capsule according to claim 51.

62. A method of reducing or eliminating symptoms of Fabry disease, comprising administering to a patient in need thereof an effective amount of a crystalline form of the compound (2R,3S,4R,5S)-1-butyl-2-(hydroxymethyl)piperidine-3,4,5-triol, wherein said compound is administered in the form of a capsule according to claim 54.

* * * * *

UNITED STATES PATENT AND TRADEMARK OFFICE
CERTIFICATE OF CORRECTION

PATENT NO. : 11,306,058 B2
APPLICATION NO. : 16/618036
DATED : April 19, 2022
INVENTOR(S) : Vitor Oliveira, Ivan Pogorelic and Jean-Paul Roduit It is certified that error appears in the above-identified patent and that said Letters Patent is hereby corrected as shown below:

In the Claims

Claim 1, Column 25, Lines 54-55:
"A crystalline form of the compound f(2R,3S,4R,5S)-1-butyl-2-(hydroxymethyl)piperidine-3,4,5-triol:"
Should read:
-- A crystalline form of the compound (2R,3S,4R,5S)-1-butyl-2-(hydroxymethyl)piperidine-3,4,5-triol:
--

Signed and Sealed this
Sixteenth Day of August, 2022

Katherine Kelly Vidal
*Director of the United States Patent and Trademark Office*